United States Patent
Streibl et al.

(10) Patent No.: US 10,429,401 B2
(45) Date of Patent: Oct. 1, 2019

(54) METHODS AND SYSTEMS FOR TUBE INSPECTION AND LIQUID LEVEL DETECTION

(71) Applicant: Beckman Coulter, Inc., Brea, CA (US)

(72) Inventors: Sebastian Streibl, Munich (DE); Jiuliu Lu, Palmetto Bay, FL (US); Bian Qian, Weston, FL (US); Melvin Ayala, Hollywood, FL (US)

(73) Assignee: Beckman Coulter, Inc., Brea, CA (US)

( * ) Notice: Subject to any disclaimer, the term of this patent is extended or adjusted under 35 U.S.C. 154(b) by 114 days.

(21) Appl. No.: 14/804,214

(22) Filed: Jul. 20, 2015

(65) Prior Publication Data

US 2016/0018427 A1    Jan. 21, 2016

Related U.S. Application Data

(60) Provisional application No. 62/027,044, filed on Jul. 21, 2014.

(51) Int. Cl.
| | |
|---|---|
| *G01F 23/00* | (2006.01) |
| *G01N 35/00* | (2006.01) |
| *G01N 33/49* | (2006.01) |
| *G01N 35/10* | (2006.01) |

(52) U.S. Cl.
CPC ....... *G01N 35/00584* (2013.01); *G01F 23/00* (2013.01); *G01N 33/49* (2013.01); *G01N 35/00732* (2013.01); *G01N 35/1016* (2013.01); *G01N 2035/1025* (2013.01)

(58) Field of Classification Search
CPC .................................................... G01F 23/00
See application file for complete search history.

(56) References Cited

U.S. PATENT DOCUMENTS

| | | | |
|---|---|---|---|
| 3,966,332 A | * | 6/1976 | Knapp ............... G01N 21/9009 356/427 |
| 5,880,364 A | | 3/1999 | Dam et al. |
| 6,227,053 B1 | | 5/2001 | Purpura et al. |
| (Continued) | | | |

FOREIGN PATENT DOCUMENTS

| | | |
|---|---|---|
| CN | 1808104 A | 7/2006 |
| CN | 2826434 Y | 10/2006 |
| (Continued) | | |

OTHER PUBLICATIONS

International Search Report and Written Opinion dated Oct. 6, 2015, for PCT Patent Application No. PCT/US2015/041180, 13 pages.

(Continued)

*Primary Examiner* — Lisa M Caputo
*Assistant Examiner* — Alex T Devito
(74) *Attorney, Agent, or Firm* — Schwegman Lundberg & Woessner, P.A.

(57) ABSTRACT

Container identification data from a container inspection unit that analyzes a container containing a liquid is combined with liquid level detection raw data from a liquid level detection unit that analyzes the container containing the liquid and a liquid level detection result is generated. The liquid level detection result is cross-checked with additional data from the container inspection unit. The result can be used to plan a route for the container in the laboratory automation system.

22 Claims, 28 Drawing Sheets

(56) References Cited

U.S. PATENT DOCUMENTS

| | | |
|---|---|---|
| 6,331,437 B1 | 12/2001 | Cohen et al. |
| 6,336,358 B1 | 1/2002 | Kishimori et al. |
| 6,403,328 B1 * | 6/2002 | Clampitt ............... G01N 15/042 435/13 |
| 6,448,574 B1 | 9/2002 | Chow et al. |
| 2005/0163354 A1 | 7/2005 | Ziegler |
| 2013/0123089 A1 | 5/2013 | Charles et al. |
| 2014/0141465 A1 | 5/2014 | Furrer |
| 2014/0233042 A1 | 8/2014 | Klinec et al. |
| 2015/0147777 A1 * | 5/2015 | Dothie ............... G01N 15/1404 435/39 |

FOREIGN PATENT DOCUMENTS

| | | |
|---|---|---|
| CN | 102687017 A | 9/2012 |
| WO | WO-2016014429 A1 | 1/2016 |

OTHER PUBLICATIONS

"Chinese Application Serial No. 201580039921.1, Office Action dated Oct. 25, 2018", w/ English Translation, 13 pgs.
"International Application Serial No. PCT/US2015/041180, International Preliminary Report on Patentability dated Feb. 2, 2017", 9 pgs.

* cited by examiner

METHODS AND SYSTEMS FOR TUBE INSPECTION AND LIQUID LEVEL DETECTION

RELATED APPLICATIONS

This application claims the benefit of and priority to U.S. Provisional Application No. 62/027,044, filed Jul. 21, 2014 and entitled "TUBE INSPECTION UNIT AND LIQUID LEVEL DETECTION COMBINED DETECTION METHOD," the entire disclosure of which is incorporated herein by reference for all purposes.

BACKGROUND

Conventional medical laboratory systems use a variety of processes when analyzing medical specimens. Some processes involve identifying medical specimens contained in sample tubes so that laboratory systems know how to process them. In some instances, the heights of component layers in a liquid need to be accurately determined so that an aliquotter can aspirate and dispense the correct amount of the liquid component.

In some instances, however, the ability to detect the level of a liquid may not be accurate. This can cause problems if too little or too much liquid or liquid component is aspirated by the aliquotter. Further, faulty information regarding the available serum volume in a sample tube may cause the analyzer probes to get stuck in e.g., gel or cruor, causing instrument downtime. This may result in monetary losses and may delay analysis results.

Embodiments of the invention address these and other problems, individually and collectively.

BRIEF SUMMARY

Embodiments of the invention relate to systems and methods for efficiently processing patient samples.

One embodiment of the invention is directed to a method comprising receiving, by a processor, container identification data from a container inspection unit that analyzes a container containing a liquid. The method further comprises receiving, by the processor, liquid level detection raw data from a liquid level detection unit that analyzes the container containing the liquid. The method further comprises determining a liquid level detection result for the liquid in the container, based at least on the container identification data and the liquid level detection raw data.

One embodiment of the invention is directed to a computer comprising a processor and a computer readable medium coupled to the processor, the computer readable medium comprises code, executable by the processor, to implement a method. The method comprises receiving, by a processor, container identification data from a container inspection unit that analyzes a container containing a liquid. The method further comprises receiving, by the processor, liquid level detection raw data from a liquid level detection unit that analyzes the container containing the liquid. The method further comprises determining a liquid level detection result for the liquid in the container, based at least on the container identification data and the liquid level detection raw data.

One embodiment of the invention is directed to a system comprising a computer, and a container inspection unit and a liquid level detection unit coupled to the computer. The computer comprises a processor and a computer readable medium coupled to the processor, the computer readable medium comprises code, executable by the processor, to implement a method. The method comprises receiving, by a processor, container identification data from a container inspection unit that analyzes a container containing a liquid. The method further comprises receiving, by the processor, liquid level detection raw data from a liquid level detection unit that analyzes the container containing the liquid. The method further comprises determining a liquid level detection result for the liquid in the container, based at least on the container identification data and the liquid level detection raw data.

One embodiment of the invention is directed to a method comprising receiving, by a processor, container identification data from a container inspection unit that analyzes a container containing a liquid. The method further comprises receiving, by the processor, liquid level detection data from a liquid level detection unit that analyzes the container containing the liquid. The receiving includes receiving a first measurement data obtained by transmitting radiation through a first portion of the container, and receiving a second measurement data obtained by transmitting radiation through a second portion of the container. The method also comprises determining a liquid level detection result for the liquid in the container, based at least on the container identification data, the first measurement data and the second measurement data.

One embodiment of the invention is directed to a computer comprising a processor and a computer readable medium coupled to the processor, the computer readable medium comprises code, executable by the processor, to implement a method. The method comprises receiving, by a processor, container identification data from a container inspection unit that analyzes a container containing a liquid. The method further comprises receiving, by the processor, liquid level detection data from a liquid level detection unit that analyzes the container containing the liquid. The receiving includes receiving a first measurement data obtained by transmitting radiation through a first portion of the container, and receiving a second measurement data obtained by transmitting radiation through a second portion of the container. The method also comprises determining a liquid level detection result for the liquid in the container, based at least on the container identification data, the first measurement data and the second measurement data.

According to various embodiments, the first measurement data is obtained by transmitting the radiation through the container at a first angle and the second measurement data is obtained by transmitting the radiation through the container at a second angle. In some embodiments, a difference between the first angle and the second angle is greater than or less than 0°. The liquid level detection unit may include a plurality of light sources. The first measurement and the second measurement may be made simultaneously. In various embodiments, the method may also include generating, by the processor, a profile map combining the first measurement data and the second measurement data. The profile map may include information about a structure of the container and the liquid contained in the container. The profile map may indicate that at least a portion of the liquid in the container is tilted. The information about the structure of the container may include location of one or more of a bottom and a top of the container, a bottom and a top of an inlay provided in the container, a bottom and a top of a label attached to the container, a positioning and an orientation of the label attached to the container, and a bottom and a top of a cap attached to the container. The information about the structure of the liquid may include one or more of a location of a bottom and top level of at least a portion of the liquid, a volume of at least a portion of the liquid, and a tilted interface between two portions of the liquid.

One embodiment of the invention is directed to a method comprising analyzing, by a liquid level detection unit, a container containing a liquid by transmitting radiation through the container containing the liquid. The method further comprises generating a signal, by the liquid level detection unit, based on the radiation traversing the container containing the liquid. The method also comprises determining, by the liquid level detection unit, container identification data for the container based at least on the signal.

In some embodiments, the method may also include providing, by the liquid level detection unit, the container data to a processor for cross-checking the container data with the additional data received from a container inspection unit. The container identification data may comprise at least one of an inner diameter, an outer diameter, a height, a cap height, an inner diameter, a cap type, a bottom shape, a false bottom (inlay) depth and a draw volume of the container.

One embodiment of the invention is directed to a computer comprising a processor and a computer readable medium coupled to the processor, the computer readable medium comprises code, executable by the processor, to implement a method. The method comprises analyzing, by a liquid level detection unit, a container containing a liquid by transmitting radiation through the container containing the liquid. The method further comprises generating a signal, by the liquid level detection unit, based on the radiation traversing the container containing the liquid. The method also comprises determining, by the liquid level detection unit, container identification data for the container based at least on the signal.

These and other embodiments of the invention are described in further detail below.

BRIEF DESCRIPTION OF THE DRAWINGS

A further understanding of the nature and advantages of the different embodiments may be realized by reference to the following drawings.

In FIGS. 7A-7B, "intensity" may refer to the light intensity observed passing through a sample and received at an LLD light detector element. "Index" may refer to a value indicating the relative movement of the tube in relation to LLD sensors (e.g., a vertical uptake of a sample tube past LLD light source/light receiver elements).

DETAILED DESCRIPTION

Figure 1:
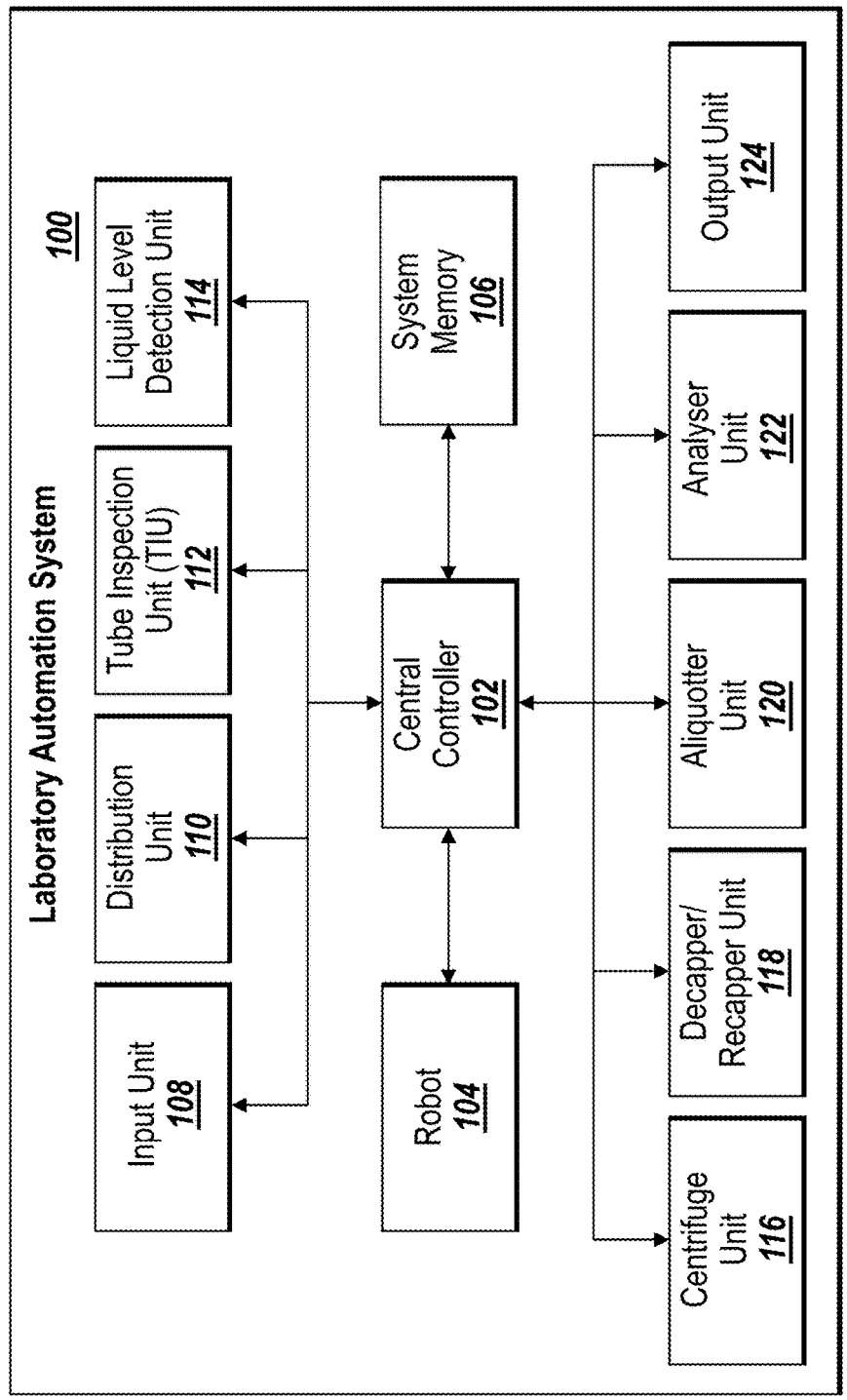
FIG. 1 illustrates a block diagram of a laboratory automation system according to an embodiment of the invention.

Embodiments of the present invention relate to laboratory systems and methods for processing patient samples. For example, specimen containers may include samples of blood or other bodily fluids on which laboratory analysis is to be performed. The analysis of a specimen may include a number of processes. For example, there may be a pre-analytical phase, an analytical phase and a post-analytical phase. The pre-analytical phase may include preparing samples for analysis. The pre-analytical phase may include several components such as an input module, a distribution area, a centrifuge, a decapper, serum indices measurement unit, an aliquotter and an output/sorter. The analytical phase may include performing the actual measurements needed to process a sample and produce results. The post-analytical phase may include preparing the sample for storage. For example, the sample container may be capped by a recapper unit and then placed in the storage.

In the pre-analytical phase, a gripper unit can be used to grip a sample container for transporting to various units in a laboratory automation system. In some instances, the robotic arm may be equipped with a camera to image the sample container for identification of the sample container during transportation. For example, Beckman Coulter's AutoMate™ 2500 series (Beckman Coulter is also assignee of the present invention) comprises a Tube Inspection Unit (TIU) that can identify a tube type, a cap type and a cap color associated with a particular sample container.

In the pre-analytical phase, sample volume and sample level detection devices are also known. Conventional sample volume or sample level detection devices are able to detect the total level of a liquid in a sample container either by an image analysis approach that analyzes 2-dimensional images acquired by a camera system, or an absorption/transmission approach that measures the absorption/transmission of different wavelengths in a light beam. Some sample volume and sample level detection devices determine a sample volume and a sample level in a sample container. In some instances, a sample volume may be calculated using an inner diameter of a sample tube. The sample volume determination may be further refined using liquid level offsets that may be dependent on the tube type based on the tube height, cap shape and cap color.

Embodiments of the invention can combine container identification data from a container inspection unit with liquid level detection raw data from a liquid level detection unit to obtain a more accurate liquid level detection result. For example, in some embodiments of the invention, information related to characterization and identification of sample containers (e.g., sample tubes) obtained from a tube inspection unit (e.g., TIU) can be used with the information obtained from a liquid level detection (e.g., LLD) unit. Illustratively, the TIU may detect a type of the sample container and may provide them to the LLD unit. The LLD unit can then use the properties in one or more algorithms for the detection or measurement of the contents of the sample container. In some embodiments of the invention, results from the LLD unit may be used to execute cross-check and calculations, leading to specialized treatment of the sample container. Embodiments of the invention can also accurately and reliably detect the characteristics of content layers, and this can reduce the failure rate of sample processing throughout the laboratory system.

In embodiments of the invention, the characteristics of samples in containers can be determined. A "container" may have any suitable shape or form. In some embodiments, the container may be in the form of a tube, which may have an aspect ratio of greater than about 3:1. Such containers may be made of any suitable material including plastic, glass, etc. They may also include a tube body (or more generically a container body) with a closed end and an open end. In some embodiments, the container may also include a cap that is structured to cover and attach to the open end of the tube body. Note that the terms "container", "sample container", "tube" or "sample tube" may be used interchangeably in this specification.

The containers may be used to contain liquids (or samples) such as serum, urine, gel, whole blood, cruor, etc. In some cases, if the sample in the container relates to blood, the container may contain whole blood (or components thereof), which may be separated into components such as plasma, buffy coat (white blood cells and platelets), and erythrocytes (includes red blood cells) as a result of centrifugation. In some embodiments, the container may be a serum separation tube which may contain a gel before any sample is placed in the container. The gel layer may separate the red and white blood cells (which may be alternatively referred to as "cruor)" from the plasma after centrifugation. The gel can be a barrier between the plasma and the red blood cells, thereby allowing the plasma to be removed more effectively for testing and related purposes. In some instances, a container may also include an additive (e.g., anticoagulant) with the sample.

In some embodiments of the invention, a container may have certain properties associated with it. Some of the properties may be related to the physical characteristics of the containers, and while others may be related to special handling during the processing of the containers. Some non-limiting examples of properties associated with the physical characteristics of a container may include inner diameters, outer diameters, a height with cap, a height without cap, a cap height, a cap geometry, a color pattern side, a color pattern top, a top rubber (inner) diameter, a cap material type, a "tube has thread" flag, a "cap pierce through" flag, a bottom shape, a false bottom (inlay), a conicity/tapering flag, a translucent flag, etc. Some other properties that may be used in processing of the sample in a container may include a decapping profile, a liquid level height offset, a "calculate no volume" flag, a cap material type, a "tube has thread" flag, a "cap pierce through" flag, a "contains gel" flag, an expected gel height, a sample type, a draw volume, cap weight, empty tube weight, tube grip height, etc.

An "inner diameter" parameter may represent an inner diameter of the container. The inner diameter may be represented in millimeters or any other suitable units. Based on the shape of the container, the inner diameter may vary at different measuring points. For example, if the container has a non-uniform shape (e.g., a conical shape), the diameter of the two ends of the container may or may not be the same. The inner diameter may also be used to determine the capacity of the container. In some embodiments of the invention, a sample volume of a container may be calculated based on the inner diameter of the container and one or more liquid levels in the container.

An "outer diameter" parameter may represent a nominal outer diameter of the container. The outer diameter may be represented in millimeters or any other suitable units. The outer diameter information may be used to determine how to grip the container (e.g., by the robot 104) and can be compared against an allowed target diameter in a rack (e.g., in the input unit 108 and/or the output unit 124 for placement of the container in the racks). The outer diameter will be bigger than the inner diameter (e.g., based on the thickness of the container).

A "height with cap" parameter may represent a nominal height of the container with a fully inserted cap. The height with cap may be represented in millimeters or any other suitable units. For example, a height with cap for a container with a container height equal to 15 mm and a cap height equal to 2 mm will be 17 mm. A parameter describing the insertion height may be used to calculate the height with cap, for example a height with cap for a container with a container height equal to 15 mm, a cap height equal to 3 mm and a cap insertion height of 1 mm will result in 17 mm (15+3−1=17).

A "height without cap" parameter may represent a nominal height of the container without a cap. The height without cap may be represented in millimeters or any other suitable units. Referring back to the previous example, the height without cap will be 15 mm.

A "cap height" parameter may represent a nominal vertical height of a cap. The cap height may be represented in millimeters or any other suitable units. Referring back to the previous example, the cap height will be 2 mm.

A "cap geometry" parameter may represent the geometry of the cap. The cap geometry may include a value representing real dimensions measured in millimeters or any other suitable units. The geometry of the cap could be cylindrical, box-like, etc.

A "color search areas" parameter may represent search areas for colors within a cap (e.g., side, top, etc.). This information may be used by a tube inspection unit to identify a cap attached to a container.

A "number of side colors" parameter may represent the number of typical colors visible from the side view of a cap that may be used for characterization. A tube inspection unit may search for the specified number to identify a cap. In some embodiments of the invention, the tube inspection unit may use the color search areas parameter together with the number of side colors parameter to identify a cap (and therefore the container type).

A "number of top colors" parameter may represent the number of typical colors visible from the top view of a cap that may be used for characterization. A tube inspection unit may search for the specified number of top colors to identify a cap. In some embodiments of the invention, the tube inspection unit may use the color search areas parameter together with the number of top colors parameter to identify a cap.

"Color pattern side" parameter may represent the color pattern for a side view of a cap that may be used for characterization. For example, there may be several patterns such as camouflage, horizontal stripe patterns, homogeneous (e.g., one single color), etc. The color pattern side parameter may be described using any suitable data type based on the TIU classification.

"Color pattern top" parameter may represent the color pattern for a top view of a cap that may be used for characterization. For example, there may be several patterns such as camouflage, circular stripe patterns, homogeneous (e.g., one single color, snap rings), etc. The color pattern top parameter may be described using any suitable data type based on the TIU classification.

A "translucent color" parameter may indicate a translucent cap or translucent tube body for a tube/cap/color combination. In some embodiments, sample containers may be classified based on the translucent color of the caps or tube body. In some embodiments, based on the translucent color parameter, different containers may have different processing in the TIU. The translucent color parameter may be described as an integer data type, an enumeration data type or any other suitable data type.

A "cap contamination possible" flag may be set to true or false based on whether the cap contamination is possible due to the opacity of the cap. For example, opacity of the cap may be influenced by the sample content which may lead to color deviations in the analysis. That is, in some cases, there is a concern that opaque caps are detected differently depending upon the specific sample in the sample container. If the "cap contamination possible" flag is set to true, the TIU detection algorithms may use this information in the decision process.

An "article number" may represent an article number of the sample container. It may include an identifier given by the manufacturer of the sample container. The article number may be represented as a data string or may be represented in any other suitable form.

A "liquid level height offset" may represent an offset which is added to a liquid level in the liquid level detection result to compensate for inaccuracies in the measured height of the content layers. For example, a sample volume may be calculated based on the measured liquid level and the inner diameter of the container. However, it may be assumed that the available sample volume is greater or less than the measured volume. Therefore, in some embodiments, based on a number of factors such as the sample type, sample container type, irregular inner diameter of the container, manufacturer of the sample container, the laboratory where the sample was collected, etc., a slight correction to the measured top liquid level (e.g., by 1-2 mm) may be made.

A "calculate no volume" flag may represent that for a certain tube/cap/color combination, sample volume need not be calculated. For example, if the "calculate no volume" flag is set to "false," a sample volume of the contents of the container may be calculated based on the liquid levels by applying a certain offset or correction. In some embodiments, the "calculate no volume" flag may be set for a specific combination of a tube/color/cap. This flag may be used by the detection algorithms in the LLD during processing of the container.

A "sample type" parameter may define an expected or defined additive in the primary sample and the liquid type expected in the container. For example, in some instances, a sample container may include an additive (e.g., Heparin, EDTA, Citrate) with the primary sample. In some embodiments, based on the sample type additive, additional inferences can be made with respect to the sample (e.g., serum, plasma, cruor, whole blood, etc.) that is potentially contained in the container. For example, if the sample container type corresponds to a hematology tube, any gel or separator layer may be excluded. In other instances, if the sample type corresponds to an EDTA tube, and a gel layer is expected, then a cruor and gel layer is expected after centrifugation. In some embodiments, the sample type parameter may be undefined for a list of possible sample types coded by a particular tube/cap/color combination. The sample type may be represented as a data string or any other suitable data type.

A "contains gel" parameter may define whether gel is part of the sample content or not. The contain gel parameter may be represented as an enumeration type or any other suitable data type. In some embodiments, the contain gel parameter may be defined as "not present", "possibly present" or "certainly present". This parameter may be used by the LLD algorithms in the detection of content layers.

An "expected gel height" parameter may represent expected gel height in the sample container. In some embodiments, the expected gel height parameter may be used in combination with the "contains gel" parameter. For example, the expected gel height parameter may be valid only when the "contains gel" parameter indicate the gel to be possible present or certainly present. This parameter may be used by the LLD algorithms in the detection of content layers. The "expected gel height" may be represented in millimeters or any other suitable units.

An "inner diameter top" parameter may define an inner diameter at the top of a sample container or sample container body. The inner diameter top may be represented in millimeters or any other suitable units. In some embodiments, the inner diameter top may be same as the inner diameter (e.g., for containers with uniform shape).

A "conicity" parameter may define the conical shape of a sample container. For example, in some embodiments, the upper inner diameter (e.g. as defined by the inner diameter top parameter) of the sample container may be different than the lower inner diameter of the sample container. In some instances, if the conicity parameter is set to "0", the inner diameter at the bottom of the sample container may be same as the inner diameter at the top of the sample container. The conicity value may be used by the LLD algorithms to determine the sample volume.

A "false bottom offset" parameter may define a height value measured from the bottom of the sample container upwards where no sample liquids or contents are expected. The false bottom offset may be represented in millimeters or any other suitable units.

A "cap pierce through" parameter may mark a cap as being suitable for pierce-through pipetting. The cap pierce through value may represent a true/false value or an enumerated value for one of several types of pierce-through caps.

A "bottom shape" parameter may define the bottom shape of a sample container. In some embodiments, the bottom shape parameter may be defined or undefined. For example, if defined, the bottom shape value may represent an enumerated value representing a type of bottom shape such as conical, round, semi-round, etc. It may be used by the LLD for cross-checking. Alternatively, if the bottom shape parameter is not defined, a bottom shape may be defined using the bottom shape parameter.

A "draw volume" parameter may define a nominal sample volume for a tube/cap/color combination. The draw volume may be represented in milliliters or any other suitable units. In some embodiments, the draw volume may be specified by the manufacturer (e.g., available in the database or marked on the sample container) and it may also depend on the amount of additive in the container. In some embodiments, the draw volume may be compared with the detected volume in the LLD to determine if the sample content is within a certain range. For example, in some instance, the draw volume of the sample content may not be enough for analysis (e.g., insufficient sample amount provided by the patient).

A "container inspection unit" may include an apparatus that is configured to identify a container. For example, in some embodiments, the container inspection unit may include apparatus to identify characteristics of a container such as a type, dimensions, expected contents, etc. and characteristics of a cap (if attached to the container). In some embodiments of the invention, a container inspection unit may be configured to identify a container based on one or more properties associated with the container as discussed above. In some embodiments, the apparatus may include a combination of hardware and software components or other suitable means to identify the container. For example, the container inspection unit may include a camera to image the container and a processor to analyze the image. Each tube type may be associated with certain properties that may be stored in a database (e.g., a tube database). Based on the colors of the cap, the cap shape and the tube height in the captured image of the tube, a tube type may be determined by referring to the database. In some embodiments, analysis of the image may include analyzing a barcode attached to the container. In embodiments of the invention, a container inspection unit includes a tube inspection unit (TIU).

"Container identification data" may include data that can identify a container. In some embodiments of the invention, such data may be determined using the container inspection unit or TIU. In some embodiments, the container identification data may include data that can be used to characterize a container based on the properties associated with the container. For example, the container properties may include a container type (e.g., tube type, height, inner and outer diameter, contains gel, draw volume, tube has thread, decapping profile, etc.), a cap type (e.g., cap material, shape, pierce through, etc.), a cap color, etc.

A "liquid level detection unit" or LLD unit may include an apparatus configured to detect a level of the liquid or a liquid component in a container. In some embodiments, depending on the contents of the container, the LLD unit may be able to detect different levels for different layers of liquids and solid substances. For example, the container may contain liquid such as serum, plasma, urine, gel, whole blood, cruor (e.g., without liquid), etc. In some embodiments, the apparatus may include a combination of hardware and software components or other suitable means to detect the content layers in the container. For example, the content layers may be determined from an image captured of the contents of the container or using an absorption and transmission measurement apparatus.

"Liquid level detection raw data" may include data captured as a result of liquid level detection of a container. Liquid level detection raw data does not include data from a tube inspection unit. In some embodiments, the liquid level detection raw data may include information related to content layers in the container. In some embodiments, such data may be captured using the liquid level detection unit. For example, liquid level raw data may contain data being indicative of a defined liquid layer height of e.g. 5 mm for a given sample in a given container. In another example, a container may include multiple layers of liquid (e.g., as a result of centrifuging) that may have a 2 mm level for cruor, 1 mm level for gel and 2 mm level for plasma.

A "liquid level detection result" may include a subsequent result of liquid level detection. A liquid level detection result may be a refined result that is derived using data from a tube inspection unit as well raw liquid level detection data. A liquid level detection result may have the same units as the liquid level detection raw data, but the liquid level detection result may be more accurate. A liquid level detection result may include a value that is determined before or after cross-checking with the results from the tube inspection unit.

"Multi-angle measurement" may include light transmission data of a container captured at multiple angles using a liquid level detection unit. The multi-angle measurements may correspond to light transmission data obtained by transmitting radiation through different portions of the container. For example, the multi-angle measurements may be captured by rotating the container with respect to a light source and light detector of the liquid detection unit. Alternatively, multiple light sources and light detectors may be used to capture the multi-angle measurements of the container. In some embodiments, the light source and the light detector may rotate with respect to the container. The multi-angle measurements may yield to information related to the geometry of the container as well as the content layers in the container.

A "profile map" may represent multi-angle measurements using visual cues e.g. shades or colors. Different values may be represented using corresponding shades or colors. For example, the profile map may include multi-angle measurements using one or more infra-red (IR) wavelength transmission, e.g., 1060 nm measurement, 1550 nm measurement and/or their quotient (i.e. the ratio of 1060 nm measurement/1550 nm measurement). The y-axis of the profile map may represent an angle index, each index corresponding to a unique angle at which signal is measured. The x-axis of the profile map may index the readings of each measurement in terms of index numbers, e.g. a signal reading index, relating to the vertical position of the tube where the beams pass through. Accordingly, x-axis shows light intensity values of transmitted light, corresponding to the vertical tube position at which light passes through the tube while the tube is transported (e.g. vertically lifted) past the emitter/receiver location.

FIG. 1 illustrates a block diagram of a laboratory automation system 100 according to an embodiment of the invention.

The laboratory automation system 100 includes a central controller 102 communicatively coupled to a robot 104, a system memory 106, an input unit 108, a distribution unit 110, a tube inspection unit (TIU) 112, a liquid level detection unit (LLD) 114, a centrifuge unit 116, a decapper/recapper unit 118, an aliquotter unit 120, an analyzer unit 122 and an output unit 124. In some embodiments, the central controller 102 may utilize a wired or wireless network to communicate with various units of the laboratory automation system 100.

The central controller 102 may be configured to operate a controlled process in the laboratory automation system 100. In some embodiments, the central controller 102 may include a central computer operated by one or more microprocessors. For example, the central controller may comprise at least one high-speed data processor adequate to execute program components for executing user and/or system-generated requests. The processor interacts with memory through signal passing through conductive conduits to execute stored signal program code according to conventional data processing techniques.

The system memory 106 may comprise any suitable type of memory device, in any suitable combination. For example, the system memory 106 may include one or more volatile or non-volatile memory devices, which can operate using any suitable electrical, magnetic, and/or optical data storage technology. In some embodiments, the system memory 106 may include a database that can store information associated with different container types (e.g., dimensions of tubes and caps, and other characteristics), liquid types (e.g., minimum volume requirement for different samples, consistency, etc.), and any other relevant information.

The robot 104 may include robotic gripper units mounted on robotic arms. A robotic gripper unit may be used to grip a sample container. For example, the robotic gripper unit may grip the sample container to place the container in a sample rack or lift it from the sample container and transport it to another unit.

The input unit 108 can accommodate a variety of sample containers, racks, prioritizations, etc. and is capable of receiving a specimen. In some embodiments, the specimens may be placed in one or more drawers in the input unit 108.

The distribution unit 110 can be configured to distribute the specimen containers from the input unit 108 to a desired sub-system of the laboratory automation system 100. For example, the robot 104 may utilize a robotic gripper unit to transport the specimen container to a distribution area. In some embodiments, before the transfer to the sub system by the robot 104, the sample container can be transferred to the TIU 112 for identification and determination of the characteristics of the sample container.

The TIU 112 may be configured to identify a container. In some embodiments, the TIU 112 may be configured to measure or extract one or more physical properties of a container such as a height, an inner diameter, a bottom shape, a cap shape, a cap color, etc. In some embodiments, the TIU 112 may comprise an imaging device such as a camera to image the container. In other embodiments, at least some of the properties of the container may be measured using one or more mechanical devices in combination with a device to identify colors. In some embodiments, a container may be identified by classifying the container based on one or more properties associated with each container type. For example, one or more properties associated with each container type may include an inner diameter, an outer diameter, a height with cap, a height without cap, a cap height, a color pattern side, a color pattern top, a top rubber (inner) diameter, a decapping profile, a liquid level height offset, a "calculate no volume" flag, a cap material type, a "tube has thread" flag, a "cap pierce through" flag, a "contains gel" flag, a bottom shape, an expected gel height, a sample type, a false bottom (inlay), a conicity/tapering flag, a translucent flag, a draw volume, empty tube weight, cap weight, etc. The TIU 112 may or may not be directly coupled to the robot 104.

FIGS. 11A-11D illustrate some examples of sample tubes that may be identified by the TIU 112 in some embodiments of the invention. Note that other designs/shapes of the sample tubes/caps are possible. The sample tubes may be with or without the caps.

Figure 11:
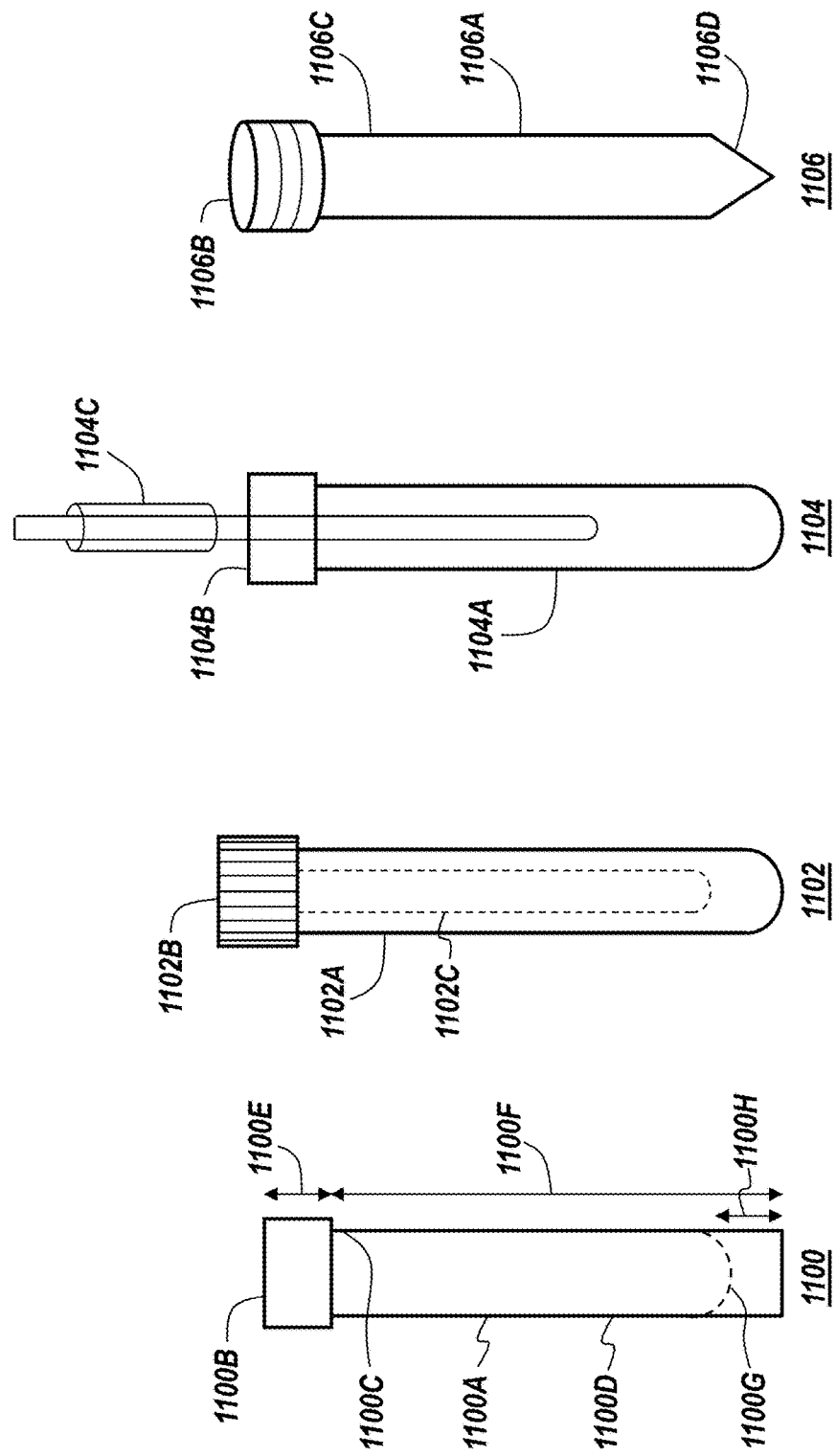
FIGS. 11A-11D illustrate some examples of sample tubes, in one embodiment of the invention.

As illustrated in FIG. 11A, a sample tube 1100 may include a tube body 1100A that may be attached to a cap 1100B. The sample tube 1100 may include an article number that may be provided by the manufacturer. The tube body 1100A is shown to include a straight bottom shape. The cap 1100B may be of any shape, color and size. In addition, the cap 1100B may be associated with certain properties such as "cap pierce through", "tube has thread" and/or a specific cap geometry. The tube body 1100A may include an inner diameter 1100C and an outer diameter 1100D. In some embodiments, the inner diameter 1100C may also be characterized as inner diameter top, e.g., for tubes with uniform shapes. A parameter 1100E may define a cap height for the cap 1100B. A parameter 1100 F may define a height without cap for the tube body 1100A. Note that in some embodiments, another parameter a height with cap may be defined or may be derived by adding the values of 1100E and 1100F. In some embodiments, the sample tube 1100 may include a false bottom 1100G as represented by a false bottom offset 1100H.

As illustrated in FIG. 11B, a sample tube 1102 may include a tube body 1102A that may be attached to a cap 1102B. The tube body 1102A may include a tube inlay 1102C. For example, the tube inlay 1102C may be a pediatric inlay, a funnel inlay, a separator, etc. The cap 1102B may also include stripe patterns. The tube body 1102A is shown to include a round bottom shape in this example.

As illustrated in FIG. 11C, a sample tube 1104 may include a tube body 1104A that may be attached to a cap 1104B. The sample tube 1104 may include a piston 1104C, e.g., to create pressure inside the tube body by pulling or pushing the piston to draw blood using a needle. The tube body 1104A is shown to include a semi-round bottom shape.

As illustrated in FIG. 11D, a sample tube 1106 may include a tube body 1106A that may be attached to a cap 1106B. The tube body 1106A is shown to include a conical bottom shape. Note that due to the conical shape of the tube body 1106A, an inner diameter top 1106C and an inner diameter bottom 1106D may not be the same. The cap 1106B is shown to include snap rings.

Sample tubes illustrated in FIGS. 11B-11D may include some or all of the physical properties as discussed with reference to FIG. 11A. In addition, the samples tubes as discussed with reference to FIGS. 11A-11D may include other properties that may be used by the TIU 112 and/or the LLD 114 during the processing of the tubes such as color search areas, number of side colors, number of top colors, color pattern side, color pattern top, translucent color, sample type, expected gel height, contains gel, conicity, draw volume, etc.

Referring back to FIG. 1, the LLD 114 may be configured to perform liquid level measurements for the sample container. In some embodiments, the LLD 114 may perform the measurement using an infrared measurement device that can scan the container vertically (e.g. by transporting the container through the light beam in vertical direction). The transmission characteristics of liquids/blood/gel can create measurement values that can allow identification of the contents as well as their heights or volumes within a container. Note that other measurement devices including imagers and devices that use ultrasonic, capacitive or conductive elements can also be used. In some embodiments, the LLD 114 may be configured to use one or more detection algorithms to determine a liquid level and/or volume of the contents of the container. The LLD 114 may or may not be directly coupled to the robot 104. Container properties such as bottom shapes, volume offsets, inner diameter, etc. may not be measured by the LLD 114 and provided to the LLD 114 by the TIU 112.

The centrifuge unit 116 may include one or more centrifuges that may be configured to separate the contents of a container into its constituents. In some embodiments, the centrifuge unit 116 may include a centrifuge controller configured to perform a number of functions associated with centrifuging.

The decapper/recapper unit 118 may be configured to decap the caps (e.g., remove the caps) of sample tubes and/or recap the caps (e.g., attach the caps) to the sample tubes. In some embodiments, the decapper and recapper functions may be performed by separate units, e.g., a decapper unit and a recapper unit. In some embodiments, recapping may be performed after the samples are analyzed and are ready for storage.

The aliquotter unit 120 may be configured to divide the contents of a container into multiple secondary samples depending on the number of samples needed for analysis.

The analyzer unit 122 may be configured to perform analysis on one or more samples. In some embodiments, the analyzer unit 122 may process the samples to produce results of the analysis. In some embodiments, the analyzer unit 122 may include a serum indices module capable of measuring a serum index of a sample.

The output unit 124 may be configured to transport the containers to racks, storage or other units as needed.

Figure 2:
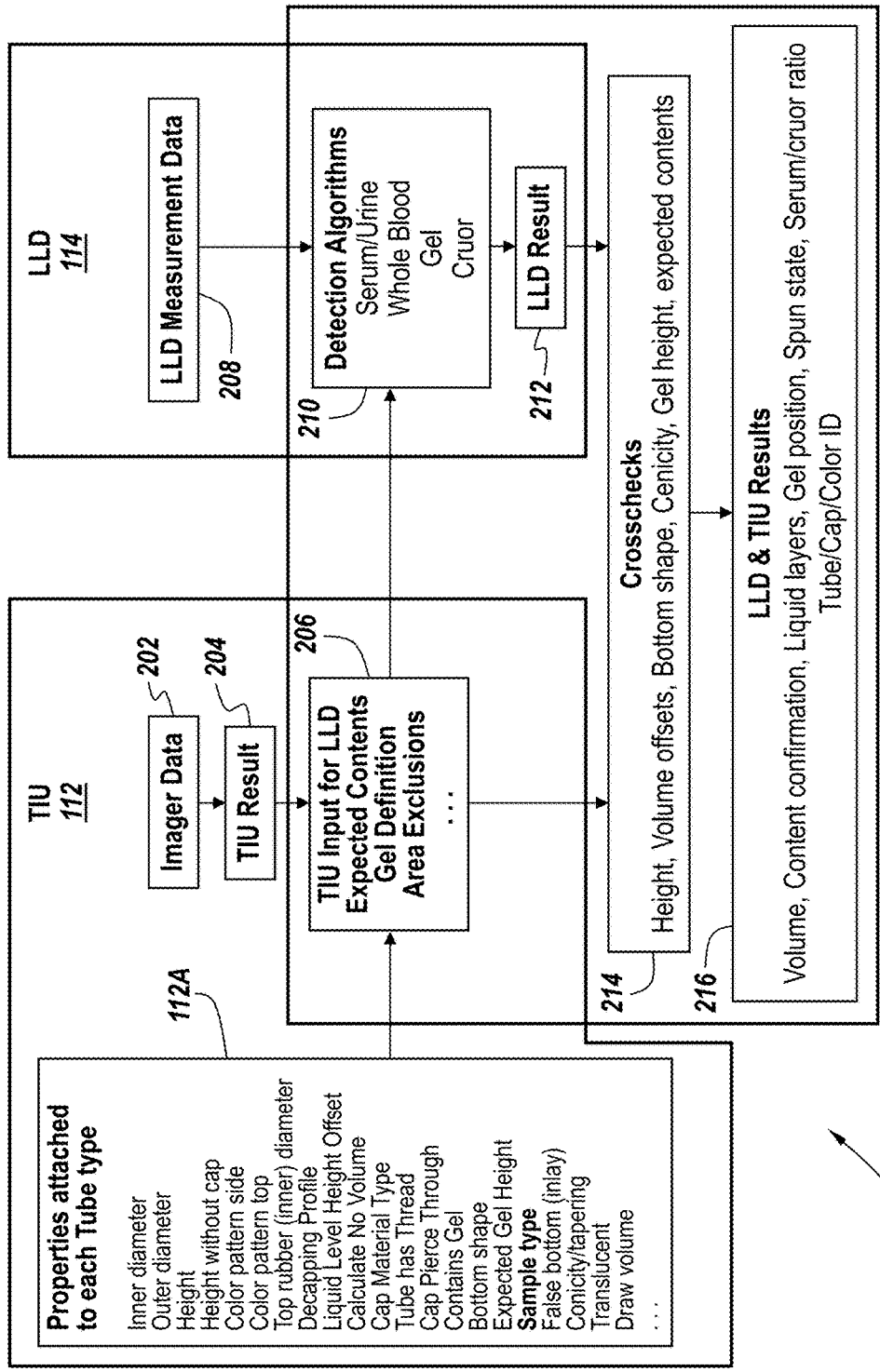
FIG. 2 illustrates a flow diagram illustrating a method to align the container type information to the liquid level measurements according to one embodiment of the invention.

FIG. 2 illustrates a flowchart illustrating a method to combine the container information received from the TIU 112 with the liquid level measurements received from the LLD 114 according to an embodiment of the invention.

A method 200 includes a process flow associated with the TIU 112 and the LLD 114.

In step 202, imager data can be obtained by the TIU 112. In some embodiments, an image acquisition device such as a camera may be used to capture an image of a container. For example, the camera may be an independent device or coupled to the robot 104. In some embodiments, a container may be identified by a barcode on the container, a cap color, a container shape, etc. The image data may be analyzed by the TIU 112 to determine information associated with the container.

In step 204, TIU results can be generated based on the imager data. For example, the TIU results may include data relating to a type of the container and its specific properties (as listed previously).

In step 206, container identification data based on the TIU results can be provided to the LLD 114. As shown in a box 112A, there may be one or more properties associated with each container type. Some non-limiting examples of the properties may include an inner diameter, an outer diameter, a height with cap, a height without cap, a color pattern side, a color pattern top, a top rubber (inner) diameter, a decapping profile, a liquid level height offset, a "calculate no volume" flag, a cap material type, a "tube has thread" flag, a "cap pierce through" flag, a "contains gel" flag, a bottom shape, an expected gel height, a sample type, a false bottom (inlay), a conicity/tapering flag, a translucent flag, a draw volume, etc. In some embodiments, properties may be linked to the identified container based on the container type/cap type/color combination in order to provide them as input to the LLD 114. In some embodiments, some of the properties in 112A can be defined by the geometry (e.g., heights, diameters, pistons, etc.), the production method (e.g., gel, conicity, etc.), or the manufacturer (e.g., predefined draw volume). Other properties that can be adjusted by the user or can be predefined may include a liquid/cell volume relation, a spun state calculation, and offset values (e.g., buffy coat) derived from the slope characteristics as described with reference to FIGS. 7A-7B. In some embodiments, additional data may be provided for crosschecking the LLD results. For example, the additional data may be associated with properties such as the container height, expected contents, volume offsets, bottom shape, conicity/tapering flag, gel height, etc. that may be cross checked against data calculated by the LLD 114 to determine a combined result.

In step 208, LLD measurement raw data may be determined by the LLD 114. For example, the LLD 144 may measure a level of changed light transmission characteristics caused by the presence of liquid, gel, cruor, etc. in the container. The measurement raw data may include a liquid level for the contents of the container without information from the TIU, and potentially a height measurement of the container. For example, the container height and the liquid level may be represented in millimeters or another suitable unit of measurement. In some embodiments, the measurements may be performed using an image acquisition device such as a camera or using light transmission based methods. The raw data may be provided to the detection algorithms. The detection algorithms may include a serum/urine detection algorithm, a whole blood detection algorithm, a gel detection algorithm and a cruor detection algorithm.

In step 210, the detection algorithms, in accordance with embodiments of the invention, may use the TIU input provided by the TIU 112 in combination with the LLD measurement data to accurately perform detection or measurement. The method may exclude areas of no interest and may enable/disable the search for specific contents. Areas of no interest could be the cap area, which can be defined by a cap height, and container inlays such as (pediatric) inlays, funnel inlays, separators, false bottoms, or pistons. The position of the areas of no interest may not be necessarily defined with a specific position. It may also be possible to only define their presence and optionally an expected dimension, which can then be used in the LLD algorithm. For example, a false bottom may be present in a particular type of sample container. The false bottom may be, for example, 2 mm from the bottom edge of the sample container. In step 210, the detection algorithms may then subtract 2 mm from detected liquid height as measured from the bottom edge of the sample container to obtain the actual height of the sample in the sample container.

In step 212, LLD results may be calculated as a result of executing the detection algorithms. The LLD results may include a liquid level. For example, the LLD results may include measurement of each content layer in the sample container. The LLD results may be provided to execute crosschecks and calculations.

In step 214, cross checks can be performed between the LLD results and the TIU results, leading to a specialized treatment of the container. The cross-check step 214 is used to determine if the LLD result 212 is erroneous, and differs from steps 206 and 210 where the TIU result is used to create a more accurate LLD result. For example, in step 214, some of the properties (e.g. height, volume offsets, bottom shape, conicity, gel height, expected contents) associated with the sample container may be obtained from the TIU 112 to cross check the results from the LLD 114 as discussed below. In one specific illustration of step 214, if the height of the tube is determined to be less than the determined liquid level, then the liquid level calculation will be characterized as being incorrect as a result of the cross-checking process.

In some embodiments of the invention, such a combined method could include one or more of the following:

Compare detected volume with draw volume: In some embodiments, the measured volume can be compared with the draw volume of the container (as obtained from the TIU) based on the container type. For example, the draw volume may be specified by the container manufacturer or a laboratory that defines the container to be used by the physicians. In some embodiments, the sample may be accepted or rejected for further processing and/or subsequent analysis based on whether the test requires the sample volume to be in specific ranges.

Calculate usable net sample volume using transition score/confidence: In some embodiments, an actual available net volume can be derived by considering offsets for unusable liquids (e.g., buffy coat, gel "eruptions" into the serum/plasma/liquid area, etc.) and container type information as provided by the TIU 112. The container type information can provide information on the physical dimensions or characteristics of the sample container, and this information can be used to help determine the net sample volume. For example, the buffy coat may be a fraction of the blood sample as a result of centrifugation (e.g., the buffy coat may be between the plasma and the red blood cells). Gel eruptions may be the presence of gel in or protrusions of gel into other layers such as serum or plasma. For example, generally, after centrifugation the gel settles down in between different liquid layers due to its density. However, based on a number of factors such as the sample type, transportation of the sample to the laboratory automation system, duration and condition of the storage of the sample, etc., the layer of the gel may not be uniform inside the container and may interfere with other layers. The determination of such offsets can be achieved by detecting layer transition characteristics, e.g. by a steep slope (see FIG. 7A) or a smooth slope (see FIG. 7B) in the transition areas of two layers, which can be used to assign a separation score or confidence level to such transitions. The confidence levels can then further be used to calculate the offset or to decide on e.g., a safety distance (as discussed with reference to FIG. 9). Within the process of deriving the actual available net volume, intermediate results can be used to calculate other information attached to a sample, such as lower serum edge, or a mark indicating that a specific sample may require manual processing (for example, due to, e.g., a tilted gel, gel eruptions, insufficient liquid for automated aliquoting, etc.).

Calculation of the spun state: In some embodiments, the sequential layer information as detected by the LLD and their height together with a definition of expected contents as provided by the TIU results (e.g. a gel layer, which may be characteristic for a certain container type) can be used to decide the spun state (spun, unspun), enabling a user to skip spinning or to repeat spinning if required. In some embodiments, transition scores as those mentioned above may also be involved in this decision. Unspun sedimented samples and spun samples can have very similar characteristics when recorded by intensity measurements in the NIR (Near Infrared Region), and the distinction between those two cases only by the relation of cruor and liquid (serum/plasma) may not be reliable.

For example, the spun state can be determined by the relation between the serum/plasma and the cruor, and if available, the location of the gel. If gel is in between the serum/plasma and cruor layer, it can be considered spun.

If according to the container type, no gel is expected to be present, the decision of the spun state may depend on several factors, for example, The relation between the serum/plasma and cruor volumes are within a defined value range. For example, volume ratio=(cruor volume)/(cruor volume+serum volume), where the result can indicate a spun state if the volume ratio <0.5.

Figure 7A:
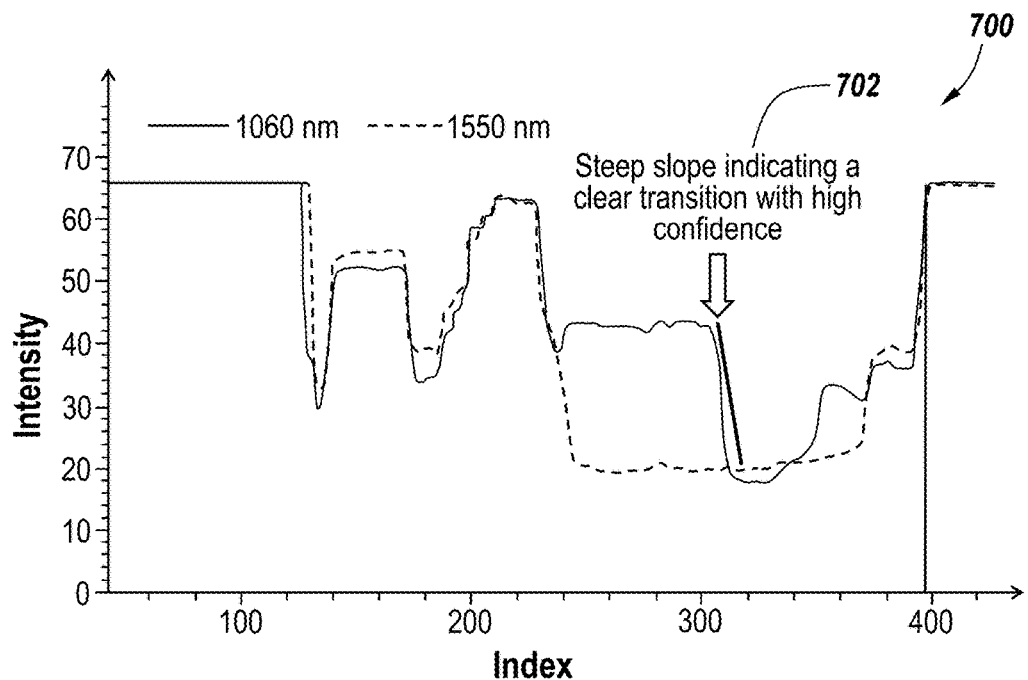
FIGS. 7A-7B illustrate a graph indicating layer transition characteristics in some embodiments of the invention.
Figure 7B:
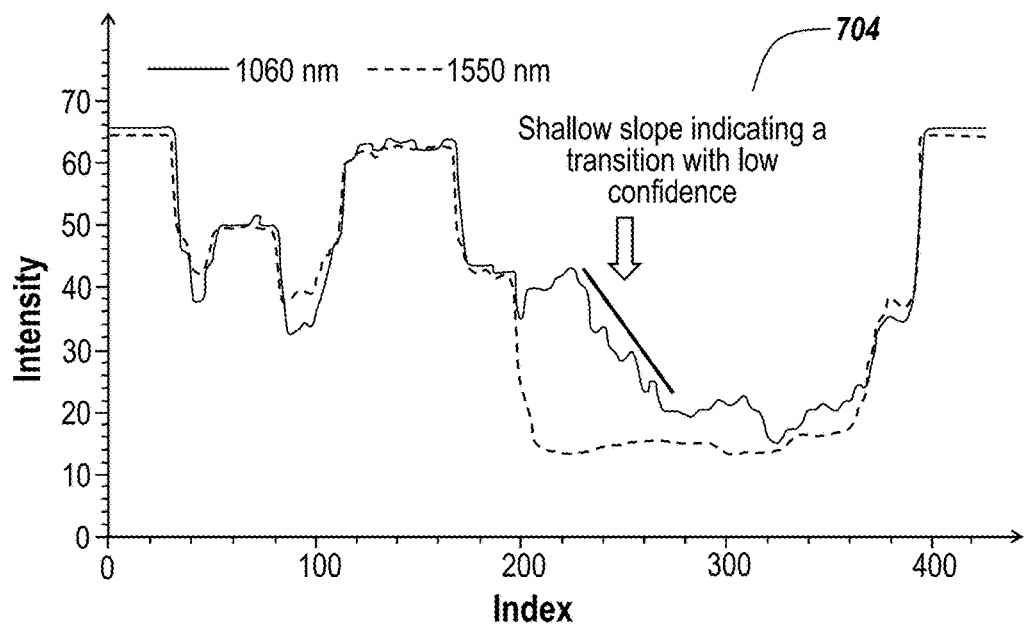

The transition from the serum to the cruor layer meets defined slope and dynamic value ranges. For example, FIG. 7A illustrates a slope 702 with high confidence and FIG. 7B illustrates a slope 704 with low confidence.

The spun state can be defined based on the container type definition (e.g. because a specific container type may not be required to be spun), the LLD measurements may not be then taken into account for the evaluation of the spun state.

Verify detected layer materials with container definition: In some embodiments, the cross check can start with this approach. The LLD algorithms can be processed one time with the container type information as input, and a second time using settings to assume all properties to be present. For example, in some embodiments, the LLD algorithms may be executed first time with only certain properties. Illustratively, based on the container definition, the gel layer or cruor may not be present. For the second time, the LLD algorithms may be executed with all the properties, e.g., with the assumption that all the layers are present. The LLD 114 may be able to detect the layers that may be actually present. The detected layers can then be used to double check the plausibility of the container type detection and definition from the TIU 112. The result can be considered safe if it is within certain tolerances the process did not reveal contradictions.

Use tube conicity for volume calculation: In some embodiments, the TIU container type definition can provide a conicity of the container in the inner structure. In some cases, the inner container walls of some container types slightly taper down to the container bottom. This is hardly detectable via mere optical means (TIU), so a container type identification (via e.g. a tube cap and outer diameter identification) can help to (indirectly) detect this feature via the TIU. This conicity can be usually inherent in the specific production method of the sample containers. Depending on the location and height of the specific layers as detected by the LLD, the conicity and the inner diameter can be used to increase accuracy of the calculated volumes.

Container breakage in centrifuge: In instances when the method is used after spinning the samples, it can be assumed that the sample is spun. The volumes of serum/plasma, separator (e.g., gel) and cruor can then be used to compare the overall volume with the previous measurement before the sample container was inserted into the centrifuge to detect container breaks, for example, when the spun sample container has less overall volume than the pre-spun sample container. In some cases, the TIU may, for example, provide information to the LLD about whether the sample tube contains a separator to obtain a more accurate sample volume determination. In another use case, liquid layer volumes can be determined after centrifugation. If at least one layer in the sample tube has an unexpectedly small volume (after the centrifugation as compared to before or as compared to the expected volume associated with the tube type information—this data may be obtained from the TIU), then it may be assumed that the tube was broken during the centrifugation process.

Liquid/cell volume relation: In instances when the method is used after spinning the samples, it can be assumed that the sample is spun. The volumes of serum/plasma, separator and cruor can then be used to calculate the relation between cruor and the liquid (plasma). As explained above, the TIU data can be used to identify the characteristics of the sample tube and this can be used to obtain a more accurate sample volume determination. According to some studies (e.g., IFCC (International Federation of Clinical Chemistry) working group on laboratory errors and patient safety), the ratio of the liquid to the total sample volume can be a key quality indicator. For example, CLSI (Clinical Laboratory Standards Institute) recommends setting the threshold for the hematocrit (cruor) percentage in a sample to 55%. For a percentage higher than 55% in an anticoagulant sample the test results could be influenced and potentially wrong.

Mutual tube and cap height verification/correction: In some embodiments, the imager in the TIU 112 can provide a height measurement of the container (capped or open). The LLD 114 can provide this information as well, e.g. using the absorption values on the laser beam(s). The imager can have a fixed field of view resulting in inaccuracies depending on the tilt of the container (towards/away from the camera, not left/right tilt) for the height measurement. Apart from the tilt, the specific optical properties of each individual sample and/or sample container can cause the top or bottom edge to be detected inaccurately by the imager. This could be the case for uncapped tubes (top edge) or for tubes with colorless liquid, causing the inaccuracy at the bottom edge:

For example, the LLD 114 can also be detecting the same edges, but in the infrared spectrum and usually with typical deflections visible in the measurement curves. In some instances, it can miss the top edge for certain uncapped containers (e.g. glass containers). In some embodiments, to enhance the measurement safety, both systems (e.g., TIU 112 and LLD 114) can use the other's measurement value for cross checks. Hence, corrections, error handling and verification of the height value can be executed in some embodiments.

The tilt of the container can also cause different height results from TIU 112 and LLD 114. In some embodiments, the value differences (e.g., of measurements from the TIU 112 and the LLD 114) can be used as a tilt indicator in instances when the fail detections on the container's upper and lower edge reason are not caused due to special optical properties of the container. In some embodiments, to avoid spills and contamination, when handling this container, a threshold (which may be dependent on the amount of tilting) can be used to trigger safety measures (e.g., reducing robot speed or torque).

Figure 8A:
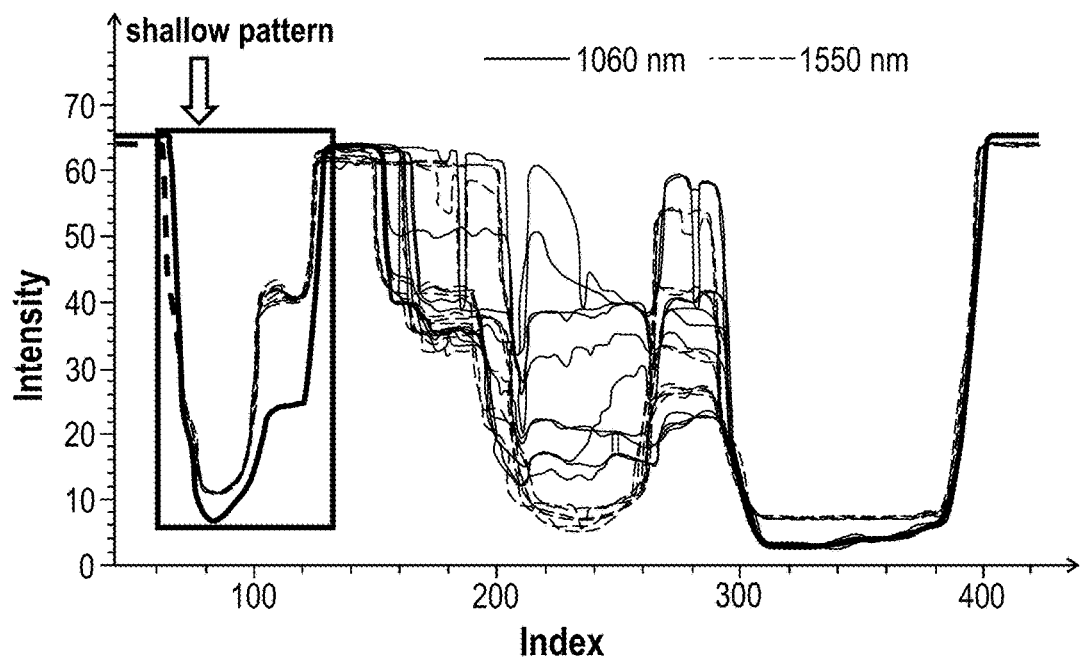
FIGS. 8A-8B illustrate patterns indicating cap characteristics in some embodiments of the invention.
Figure 8B:
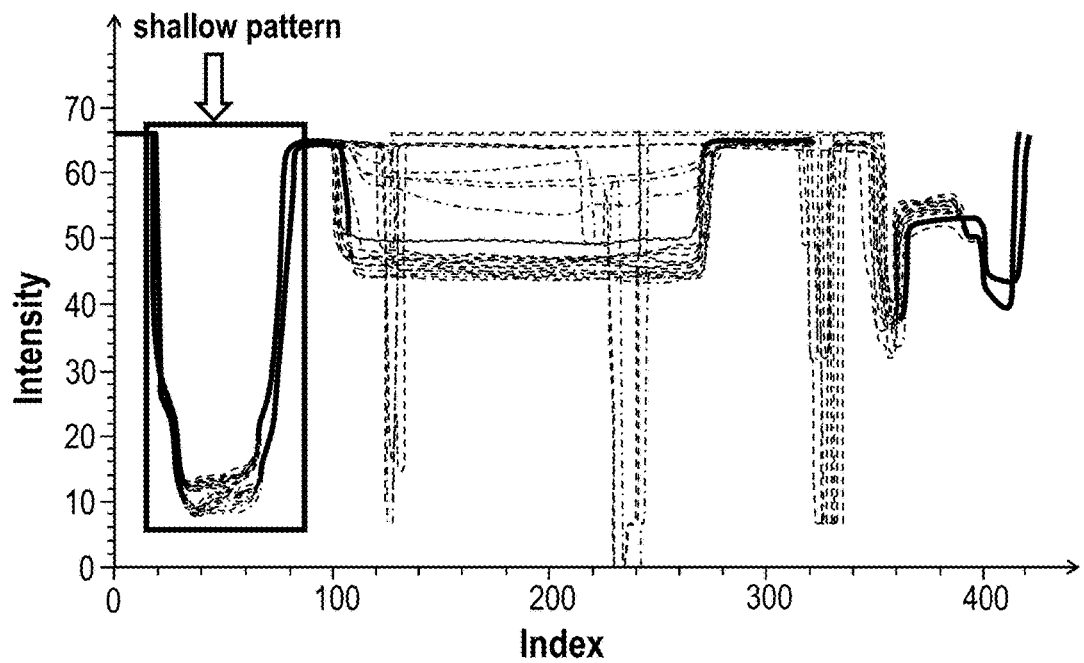

Cap material characterization: The exclusion area defined by a cap height parameter from the TIU 112 can be inspected by the LLD 114 to search for material specific patterns. In some embodiments, the TIU 112 alone can detect a cap type using cap shape and color characteristics. The cap materials and inner structure can cause specific absorption characteristics, which can be identified e.g. using Pearson's correlation coefficient to be above a specific threshold, pattern recognition, or relative thresholds on the local minima and maxima of measurement intensities. For Pearson's correlation coefficient, the test sample could be used to calculate its correlation coefficient with one or more reference datasets. FIGS. 8A and 8B illustrate two examples of one cap type and its stability across several measurements. The confirmation of a specific cap material and type via the LLD can be used in the decapping process, as the grip force and grip position values may depend on the material and inner structure of the cap.

Recap verification: In some embodiments, the TIU 112 and LLD 114 results can be used to verify a proper decapping and recapping process. On the way through the lab, the sample may pass a LLD measurement device (e.g., LLD 114) several times, but may not necessarily pass a TIU 112 with fully configured detection. In most instances, the TIU 112 may be able to confirm the cap presence or absence. However, in some instances, e.g. in systems where the system output robot may be equipped with a liquid level detection unit, when only the LLD 114 may be available, the previously identified TIU 112 parameters can be combined with a new LLD result to calculate the height difference between the identified tube without a cap and the LLD height measurement result, which can correlate with the summed heights of the "recapping" cap and the open tube. Applying tolerances to this calculation may allow one to detect recapping failures e.g. due to inner pressure which can push the cap out of the tube, making it unsuitable e.g., for further transporting or archiving.

Transition edge verification: In some embodiments, results describing the start (upper) and end (lower) of layers (e.g., urine, serum, plasma, retrospinal fluids, cruor, gel, container bottom, pistons, etc.) can be calculated in relation to the top and bottom surface of the container. For example, due to transportation of the sample or due to centrifuging or due to other reasons, the transition ("edge") of a layer (e.g., serum to gel to cruor) may not be clearly detectable. In such instances, LLD measurements may be performed at different angles (e.g., by rotating the sample container within the LLD equipped robotic gripper) to verify the levels of detected layers. In some embodiments, it may be possible to verify the transition of those layers using the following exemplary methods in some systems:

Using a LLD equipped robot: In some embodiments, the detected layer transition edge within a sample container can be positioned at the same level as the LLD detector arrangement (510), and a measurement may be executed while the container is rotated. The resulting curve can reveal a constant feature across the radial sector or full circle, which can be interpreted as a verification/confirmation of the detected layer transition edge. Alternatively, the resulting curve can reveal inconsistent or interrupted features, which may mean that the previously detected transition edge is not constant over the full rotation. In the latter case, the edge cannot be confirmed, but can be corrected by moving the sample container higher or lower in relation to the LLD detector arrangement and repeating the same rotational measurement again. Within a certain range, the detected edge can be corrected for proper usage in the lab.

The problem that is addressed is e.g., a tilted gel or an off-centered gel eruption: after the first measurement (e.g., before the edge verification is executed), the LLD result can provide the "lower serum edge" value for serum/plasma. Due to the design of infrared measurements executed through transmission (one beam is directed through the middle of the tube), the result may be based upon one measurement angle only (e.g., the tube may be tilted or, if a tilted/inclined layer is present, positioned in such a rotational position/angle within the gripper arm that the light beam can pass though the sample liquid without being impeded, while in another rotational orientation, the beam could be blocked by the upper part of the inclined layer or an off-centered gel eruption). When a tilted gel is detected the "lower serum edge" value, may be increased to avoid, when pipetting such samples with tilted gel or "gel eruptions", a possible obstruction of the pipette in the gel, thus requiring maintenance, other user interaction or even sample loss. As compared to simple generic offsets that may be applied without detailed information regarding the nature of the specific layer transition edge (tilt, eruption etc.), the proposed improved offset calculation can help using the available liquid efficiently (especially important for e.g. pediatric samples, where little volume may be available).

In some embodiments, imaging devices can also be used to verify or correct the detected layer edges. In the existing systems, it may be possible to execute a post processing step on the available TIU image using the detected (LLD) transition edges. The imaging algorithms could e.g. search for features (e.g., color, brightness, etc.) in the detected area(s).

This method would e.g., avoid an additional pick and place operation (e.g., transport container from position A to position B) of the test sample to acquire this information.

In some embodiments, a dedicated device (e.g., a simple z-axis gripper with scanner) may be used that is able to scan the detected transition edge(s) circumferentially. However, this may be time consuming. In some embodiments, it may be preferred to have a gripper robot move the sample to the desired position as described in the TIU and LLD examples.

Figure 9:
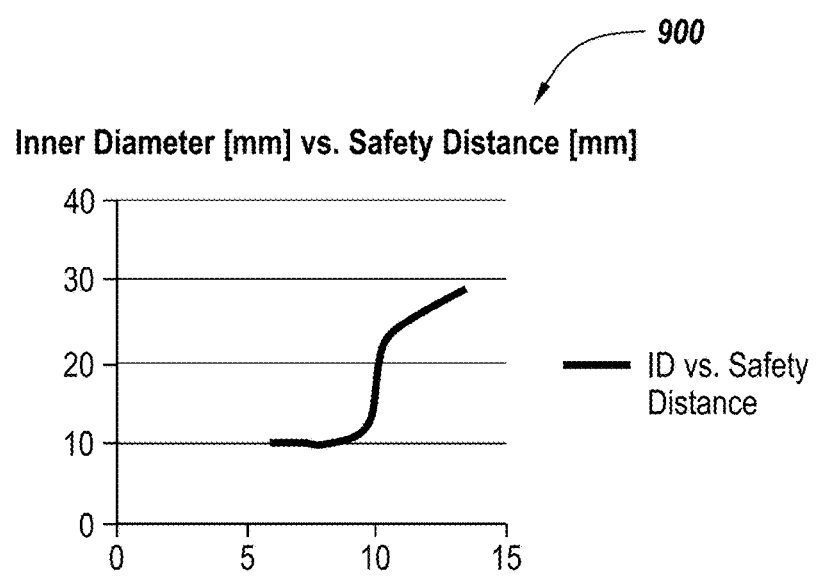
FIG. 9 illustrates a graph indicating safety distance as a function of the inner diameter of a container, in some embodiments of the invention.

Critical fill level handling: In some embodiments, the top liquid/blood level in the container in relation to the top edge of the container may have an influence on processing of the container in the lab. For example, directly affected functions may be a) robot speed and track suitability, b) routing decisions, c) decapping and d) recapping. In some embodiments, the input parameters provided by the TIU 112 that may be necessary to make a decision by the LLD 114 for safely handling the probe may be 1) a top liquid level in mm, 2) an overall height of the tube with the cap, 3) an overall height of the tube without the cap, and 4) the inner diameter. In some embodiments, a volume value may be used in addition. FIG. 9 illustrates an example for safety distance as a function of the inner diameter of the container, in one embodiment of the invention.

Robot speed: In some embodiments, the robot maximum acceleration can be adjusted using the distance between the top container edge and the top liquid/blood level, called safety distance. Depending on the inner diameter of the container, the horizontal acceleration of the upright container may cause liquid spills. The inner diameter can be proportional to the safety distance. In addition, fluid adhesion forces and surface tension of the fluids may also have a small influence. In some embodiments, the calculation method can also be used for the container transport/track system. However, due to the different acceleration profile (no S-Curve) and the different rotation points on a curved track (e.g., compared to a container held in a gripper robot, and the possible resulting tilts), the overall height of the container can influence thresholds and decisions whether a container can be safely placed on the track system.

Routing decisions: In some embodiments, in the decision rules to send a container on a specific route, e.g., a route involving decapping, recapping, aliquoting, analysis, routing to different workplaces such as error workplace, external shipping, etc., the four above named input parameters may be used to reject a sample for processing due to functional conflicts. For example, Analyzers can have specified maximum fill levels (e.g., due to integrated transport mechanisms).

The decapping step may turn a closed container into an open container. As this information may not be available for a single robot, the routing can decide to send the container to the error workplace, because it would be too full for correct processing after decapping.

Recapping can only occur if the used cap (e.g., push cap, screw cap, etc.) is suitable for the top liquid level. The top liquid level may be possibly reduced due to analysis steps/pipetting some liquid before the recapping is done. Recapping with too much liquid in the container may cause spills and contamination. In some embodiments, a possible solution could be to create an extra aliquot to reduce the top liquid level to make recapping possible, and avoiding additional manual processing.

Decapping: In some embodiments, if the routing decision does not consider decapping restrictions, the top fill level and the safety distance can be considered in adjusting the decapping profile. In instances, where a standard decapping profile could remove a cap quickly by applying relatively big forces and speed, such forces, speed and motions could be adjusted, i.e. reduced—considering the safety distance—to avoid spills and contamination during decapping.

Recapping: In some embodiments, if the routing decision does not consider recapping restrictions, the top fill level and the safety distance can be used to reject the recapping request, depending on the type of recapping (e.g., screw cap, push cap, etc.).

Referring back to FIG. 2, in step 216, LLD and TIU results are generated as a result of crosschecking. In some embodiments, the LLD and TIU results may include a net volume, content confirmation, liquid layers, a gel position, a spun state, a serum/cruor ratio, a tube/cap/color ID, etc.

Figure 3A:
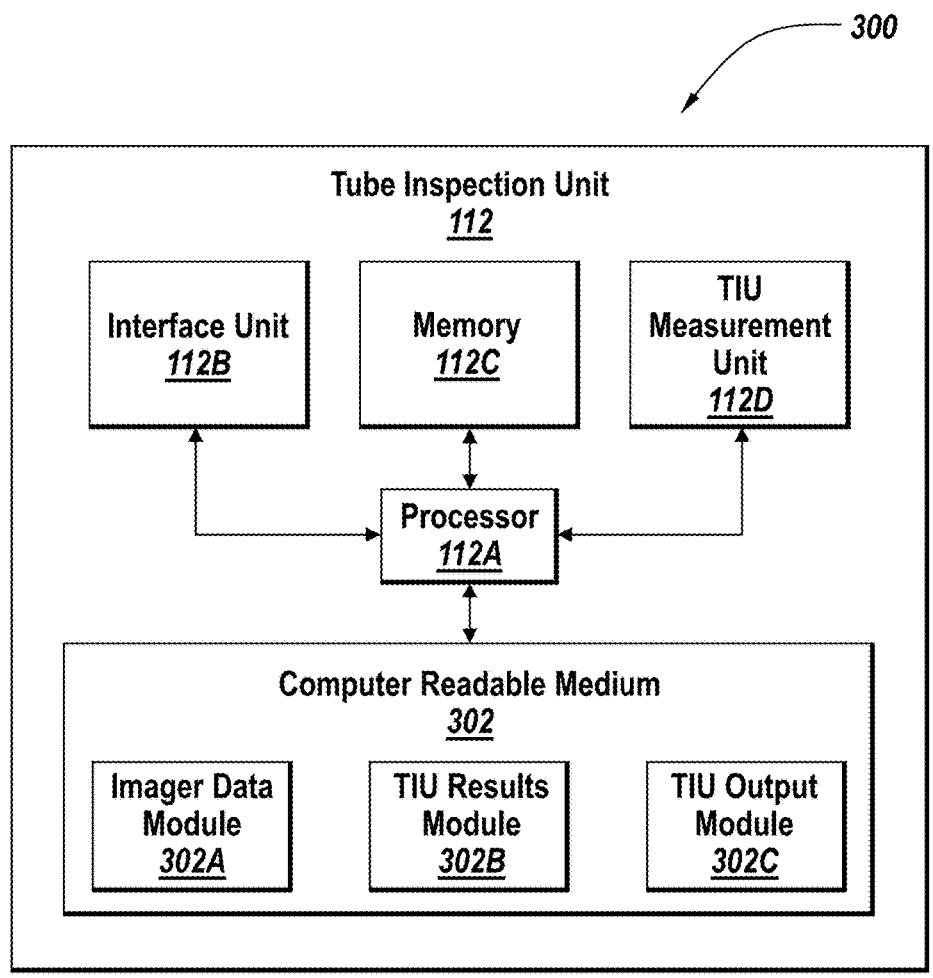
FIG. 3A illustrates some components of a tube inspection unit, in one embodiment of the invention.

FIG. 3A illustrates some components of a container (e.g., tube) inspection unit, in one embodiment of the invention.

The TIU 112 may include a processor 112A coupled to an interface unit 112B, a memory 112C, a TIU measurement unit 112D and a computer readable medium 302.

The processor 112A may comprise one or more microprocessors that can function separately or together to cause various components to operate. The processor 112A may be configured to execute instructions stored in the computer readable medium 302.

The interface unit 112B may be configured to interface with various components of the laboratory automation system 100. For example, the interface unit 112B may utilize a wired or wireless network to communicate with the central controller 102, the LLD 114, the robot 104 and other components of the laboratory automation system 100.

The memory 112C may be any suitable memory and may comprise one or more volatile or non-volatile memory devices. In some embodiments of the invention, the memory 112C may store one or more properties associated with various container types. For example, the memory 112C may include an inner diameter, an outer diameter, a height, a height without cap, a color pattern side, a color pattern top, a top rubber (inner) diameter, a decapping profile, a liquid level height offset, a "calculate no volume" flag, a cap material type, a "tube has thread" flag, a "cap pierce through" flag, a "contains gel" flag, a bottom shape, an expected gel height, a sample type, a false bottom (inlay), a conicity/tapering flag, a translucent flag, a draw volume, etc.

The TIU measurement unit 112D may be configured to perform measurements of the container. For example, in some embodiments, the TIU measurement unit 112D may be configured to measure or extract one or more physical properties of a container such as a height, a width, a bottom shape, a cap shape, a cap color, etc. In some embodiments, the TIU measurement unit 112D may comprise an imaging device such as a camera to image the container. In other embodiments, the TIU measurement unit 112D may be configured to measure at least some of the properties of the container using one or more mechanical devices in combination with a device to identify colors.

The computer readable medium 302 may comprise code that may be executable by the processor 112A to implement embodiments of the invention. The computer readable medium 302 may include an imager data module 302A, a TIU results module 302B and a TIU output module 302C.

The imager data module 302A may be configured to receive data captured using the TIU measurement unit 112D. For example, the imager data module 302A may include data related to the container and cap dimensions, volume, contents, etc.

The TIU results module 302B may be configured to determine characteristics of the container based on the image data. For example, the TIU results module 302B may determine a container height, a cap height, bottom areas, expected contents, inlays, etc.

The TIU output module 302C may be configured to provide container identification data to the LLD 114. In some embodiments, the TIU output module 302C may utilize properties attached to each container type for providing container identification data as an input to the LLD 114.

Figure 3B:
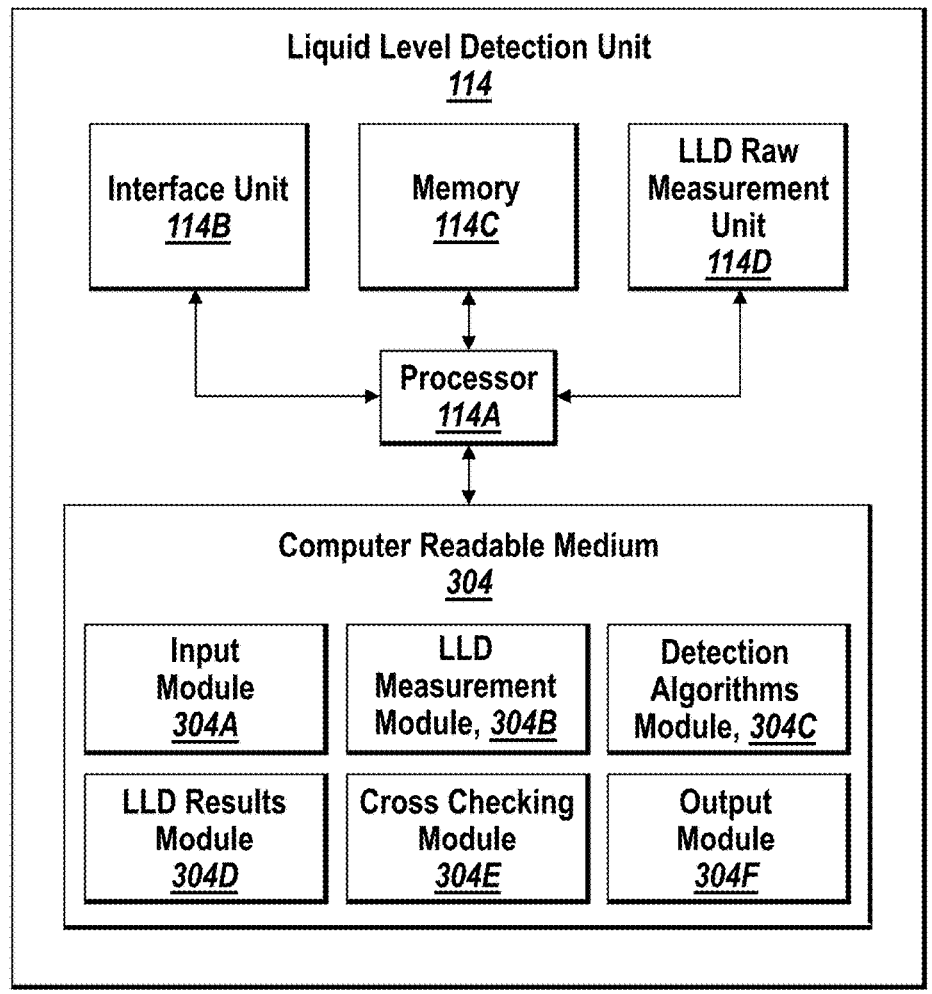
FIG. 3B illustrates some components of a liquid level detection unit, in one embodiment of the invention.

FIG. 3B illustrates some components of a liquid level detection unit, in one embodiment of the invention.

The LLD 114 may include a processor 114A coupled to an interface unit 114B, a memory 114C, an LLD raw measurement unit 114D and a computer readable medium 304.

The processor 114A may comprise one or more microprocessors that can function separately or together to cause various components to operate. The processor 114A may be configured to execute instructions stored in the computer readable medium 304.

The interface unit 114B may be configured to interface with various components of the laboratory automation system 100. For example, the interface unit 1124 may utilize a wired or wireless network to communicate with the central controller 102, the TIU 112, the robot 104 and other components of the laboratory automation system 100.

The memory 114C may be any suitable memory and may comprise one or more volatile or non-volatile memory devices. In some embodiments of the invention, the memory 114C may store one or more properties associated with various liquid types.

The LLD raw measurement unit 114D may be configured to measure the height of the container and a liquid level of the container to provide liquid level detection raw data. In some embodiments, the LLD raw measurement unit 114D may perform the measurement using an infrared measurement device that can scan the container vertically (e.g. by transporting the container through the light beam in vertical direction). The transmission characteristics of liquids/blood/gel can create measurement values that can allow identification of the contents. Note that other measurement devices such as an imager or using ultrasonic, capacitive or conductive means are also possible.

The computer readable medium 304 may comprise code that may be executable by the processor 114A to implement embodiments of the invention. The computer readable medium 304 may include an input module 304A, an LLD measurement module 304B, a detection algorithms module 304C, an LLD results module 304D, a cross checking module 304E and an output module 304F.

The input module 304A may be configured to receive input data from other units such as the TIU 112. In some embodiments, the input data may include data related to characteristics and identification of the container, e.g., container identification data.

The LLD measurement module 304B may be configured to analyze liquid level detection raw data from the LLD raw measurement unit 114D. For example, the liquid level detection raw data may be data related to a liquid level of the container, etc.

The detection algorithms module 304C may be configured to execute one or more algorithms on the liquid level detection raw data and the container identification data provided by the TIU 112. For example, the detection algorithms module 304C may include one or more of a serum/urine detection algorithm, a whole blood detection algorithm, a gel detection algorithm and a cruor detection algorithm.

The serum/urine detection algorithm may detect serum or urine in the sample. Any known methods to detect whether the sample is a serum or urine sample may be used.

The gel detection algorithm may detect gel in the sample. For example, the gel detection algorithm may detect the gel using any suitable algorithm.

The cruor detection algorithm may detect cruor in the sample. For example, the cruor may be detected using any suitable algorithm.

The whole blood detection algorithm may detect whole blood in the sample. For example, the whole blood may be detected using any suitable algorithm.

The LLD results module 304D may be configured to determine a liquid level detection result based on execution of the algorithms. In some embodiments, the LLD result may include a liquid level (e.g., height in millimeter) for all the content layers. For example, the LLD result may include that the sample includes 5 mm of serum layer, 1 mm of gel layer and 4 mm of cruor layer.

The cross checking module 304E may be configured to cross check the LLD results with the additional data provided by the TIU 112. In some embodiments, the cross checking module 304E may compare the measured volume from the LLD 114 with the draw volume provided by the TIU 112. In some instances, if the measured volume is not same as the draw volume, the sample may be flagged for manual inspection or being not suitable for analysis. In some embodiments, the cross checking module 304E may calculate a usable net sample volume using transition score/confidence based on the container type information from the TIU 112 and considering offsets for unusable liquids (e.g., buffy coat, gel "eruptions" into the serum/plasma/liquid area, etc.) from LLD 114. In some embodiments, the cross checking module 304E may determine a spun state based on the sequential layer information and their height together with a definition of expected contents from the LLD 114 and/or the container type definition from the TIU 112. In some embodiments, the cross checking module 304E may verify detected layer materials with container definition based on the liquid level detection results from the LLD 114 and container identification data from the TIU 112. In some embodiments, the cross checking module 304E may calculate sample volumes based on tube conicity information provided by the TIU 112. In some embodiments, the cross checking module 304E may be used to determine if the spun sample container has less overall volume then the pre-spun sample container to detect container breaks in centrifuge. In some embodiments, the cross checking module 304E may determine a ratio of the liquid to the total sample volume. In some embodiments, the cross checking module 304E may perform mutual tube and cap height verification/correction based on the container identification data from the TIU 112 and liquid level detection data from the LLD 114. In some embodiments, the cross checking module 304E may perform the cap material characterization based on the container identification data from the TIU 112. In some embodiments, the cross checking module 304E may verify a proper decapping and recapping process based on the container identification data from the TIU 112 and liquid level detection data from the LLD 114. In some embodiments, the cross checking module 304E may perform transition edge verification and critical fill level handling as described previously with reference to FIG. 2

The output module 304F may be configured to provide outputs to various units of the laboratory automation system 100. For example, the output module 304F may provide a combined result once the cross-checking is performed by the cross checking module 304E on the data from the container inspection unit and the liquid level detection unit.

Figure 4:
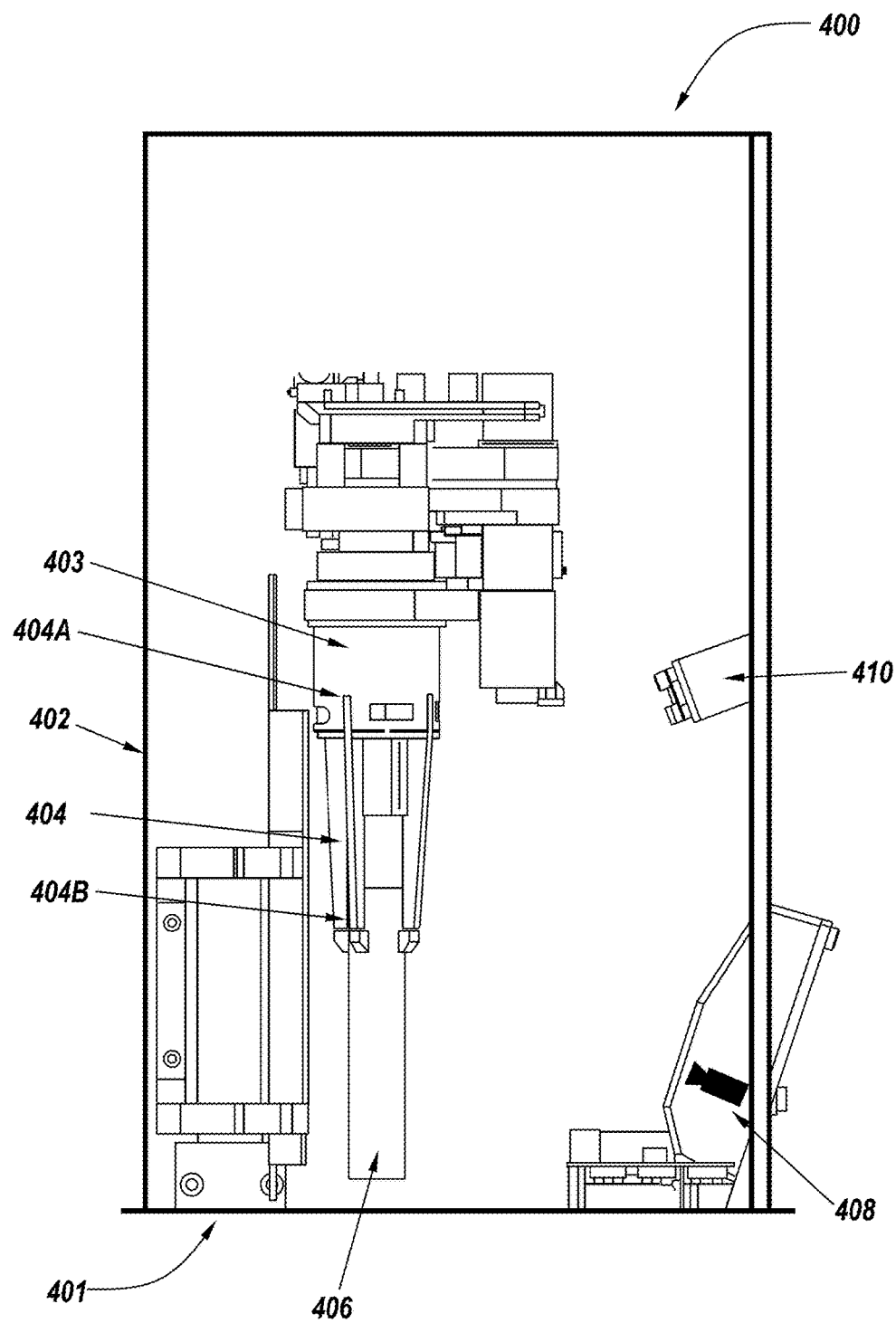
FIG. 4 illustrates an exemplary system including a Tube Inspection Unit (TIU) and a Liquid Level Detection Unit (LLD).

FIG. 4 illustrates an exemplary system (e.g. a robot) 400 with a Tube Inspection Unit (TIU) 408 and a Liquid Level Detection Unit (LLD) 401.

The robot 400 can include a chamber 402. The TUI 408 including a camera can be accommodated in the chamber 402, which has few and, if possible, no optical reflections. The TUI 408 can be aligned with and focused on a sample container 406 containing liquid. An illumination source 410 may provide light to the sample container 406 so that the TUI 408 can take a picture of the sample container 406.

The TUI 408 can include a still camera, a color image camera, a video camera, a spectral camera or the like. A color image camera, for example, a 3CCD video camera, may be used. The settings of the color camera, such as focusing, white balance, diaphragm setting, filling-in, can be permanently preset or adjustable. For example, they can be adjusted with the aid of image evaluation software, as in when the data reported by the image evaluation software to the control software are of reduced quality with reference to store reference data. An algorithm can be used to calculate the sample level and/or volume using known data, such as the type of sample container used, the type of sample, etc.

As shown in the figure, the TUI 408 can be inclined to optimize its view of the sample container 406. The sample container 406 information can be recorded with comparatively few optical reflections with the aid of this measure.

The LLD 401 may include a robotic arm 403 having multiple prongs (e.g. pincers) 404. A proximate end 404A of each prong 404 may be coupled to the robotic arm 403. Distal ends 404B of the prongs 403 may hold (e.g. carry) a sample tube 406 containing a sample. The LLD 401 may measure the light signal (emitted by the illumination source 410) that passes through the sample tube 406 at a single angle that is chosen randomly. That is, the light signal may pass through a single portion of the tube 406.

As an alternative to the liquid level detection device using a camera unit, the liquid level detection may also be accomplished by the use of another type of image acquisition device such as a device that has laser diodes with a defined wavelength and analysis algorithms to evaluate the absorption spectra. A laser diode beam can be focused on sections of the sample tube, and absorption and transmission measurement of different wavelengths of the focused beam can be measured by a light sensitive detector. An analysis algorithm can then use the measurements to provide the liquid level and volume.

Figure 5:
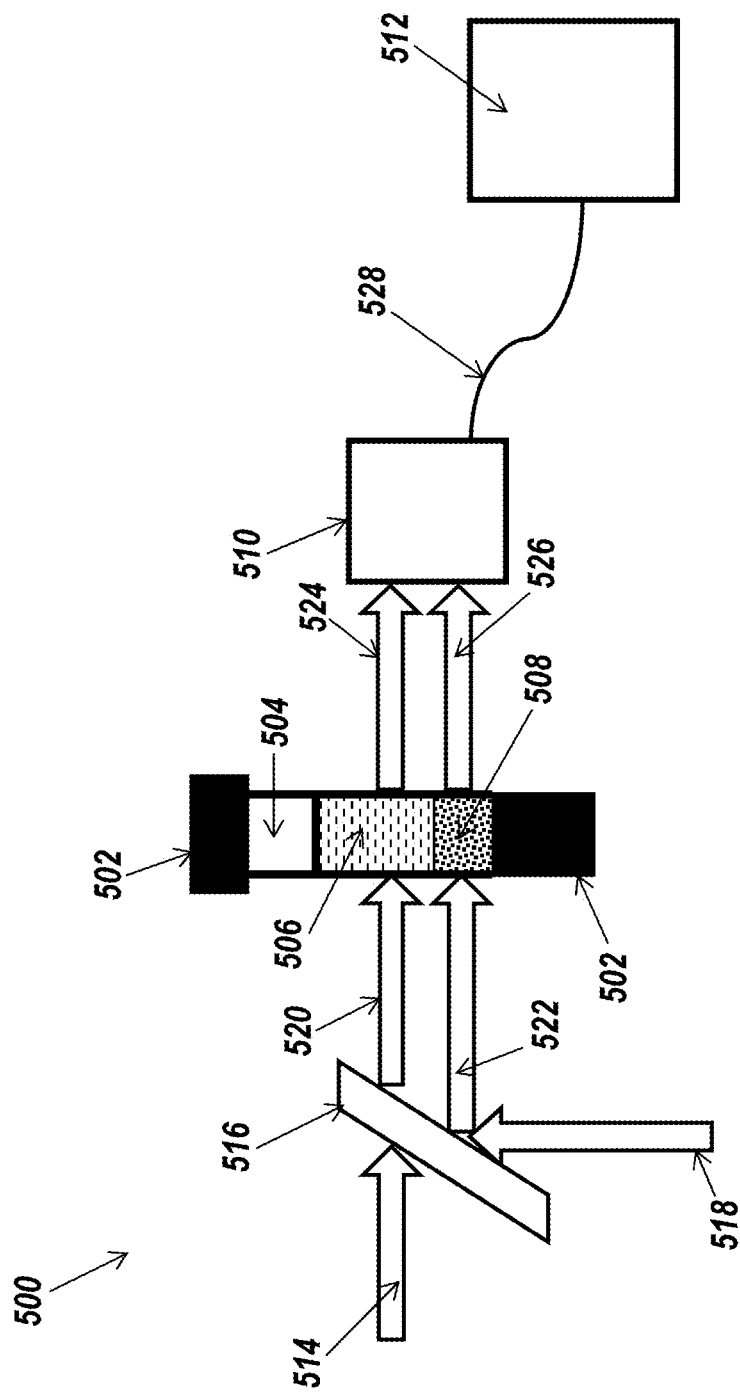
FIG. 5 illustrates an example of sample level detection utilizing the analysis of absorption and transmission curves at distinct wavelengths.

FIG. 5 illustrates an example of sample level detection utilizing the analysis of absorption and transmission curves at distinct wavelengths. In instances in which blood samples are provided with the sample tube, the system may additionally be able to detect the distinct levels of serum, plasma, or blood-cake in the sample.

In FIG. 5, a portion of an operable fluid sample interrogation system is depicted generally at 500. A first source of radiation 514 (with a second source of radiation 518 turned off) is arranged to apply a first radiation having a first characteristic wavelength (e.g., 980 nm) to beam combiner 516, which directs the first emitted radiation 520 toward a location on the sample tube 502. The first transmitted radiation 524 can be detected by a detector, such as illustrated photo diode and amplifier arrangement 510. The detector may be an example of at least a part of an image acquisition device. A signal 528, corresponding to the intensity of first transmitted radiation 524 can then be stored and/or manipulated in comparison structure, such as programmable integrated circuit 512, or a computer. The second source of radiation 518 (with the first source of radiation 514 turned off) is arranged to apply a second radiation having a second characteristic wavelength (e.g., 1050 nm) to beam combiner 516 at a slightly shifted position as the first emitted radiation 520, which directs the second emitted radiation 522 parallel to the beam path of first emitted radiation 520 toward a slightly different location on the sample tube 502. The second transmitted radiation 526 can be detected by the same detector, such as illustrated photo diode and amplifier arrangement 510. The signal 528, corresponding to the intensity of second transmitted radiation 526 can then be stored and/or manipulated in comparison structure, such as programmable integrated circuit 512, or a computer.

FIG. 5 further depicts a sample tube that is being measured and analyzed using the wavelength process, for example, by the LLD raw measurement unit 114D. As shown, serum 506 and gel 508 can be mostly transparent to visible light while red blood cells 502 can be substantially opaque. Further, gel 508 can be transparent to infrared light while red blood cells 502 and serum 506 can be substantially opaque. Accordingly, when the sample tube 502 has gel 508 to separate the serum 506 and red blood cells 502, it may be possible just using infrared light to "see through" different sections. The infrared light reading is strong when the infrared light beam passes through air 504, drops when the infrared light beam is directed toward the serum, is relatively strong when directed toward the gel 508, and drops again when directed toward the red blood cells 502. This analysis performed by the analysis tool can allow for the measurement of the sample level/volume of the sample.

In some embodiments, the liquid level detection unit 500 can be combined with a robotic arm (e.g., coupled to the robot 104) with or without a tube inspection unit (e.g., TIU 112). For example, in some embodiments, a sample tube is picked by a robotic gripper and is transported vertically past the at least two infrared light sources of the LLD. The light passes through the center of the tube. On the side of the tube opposite the light sources, a detector collects the transmitted light of the different wavelengths. An addition a camera (TIU) can capture at least one image of the tube and the cap. The at least one image can be capture from the side of the tube and from above the tube (e.g. via a mirror).

Figure 6:
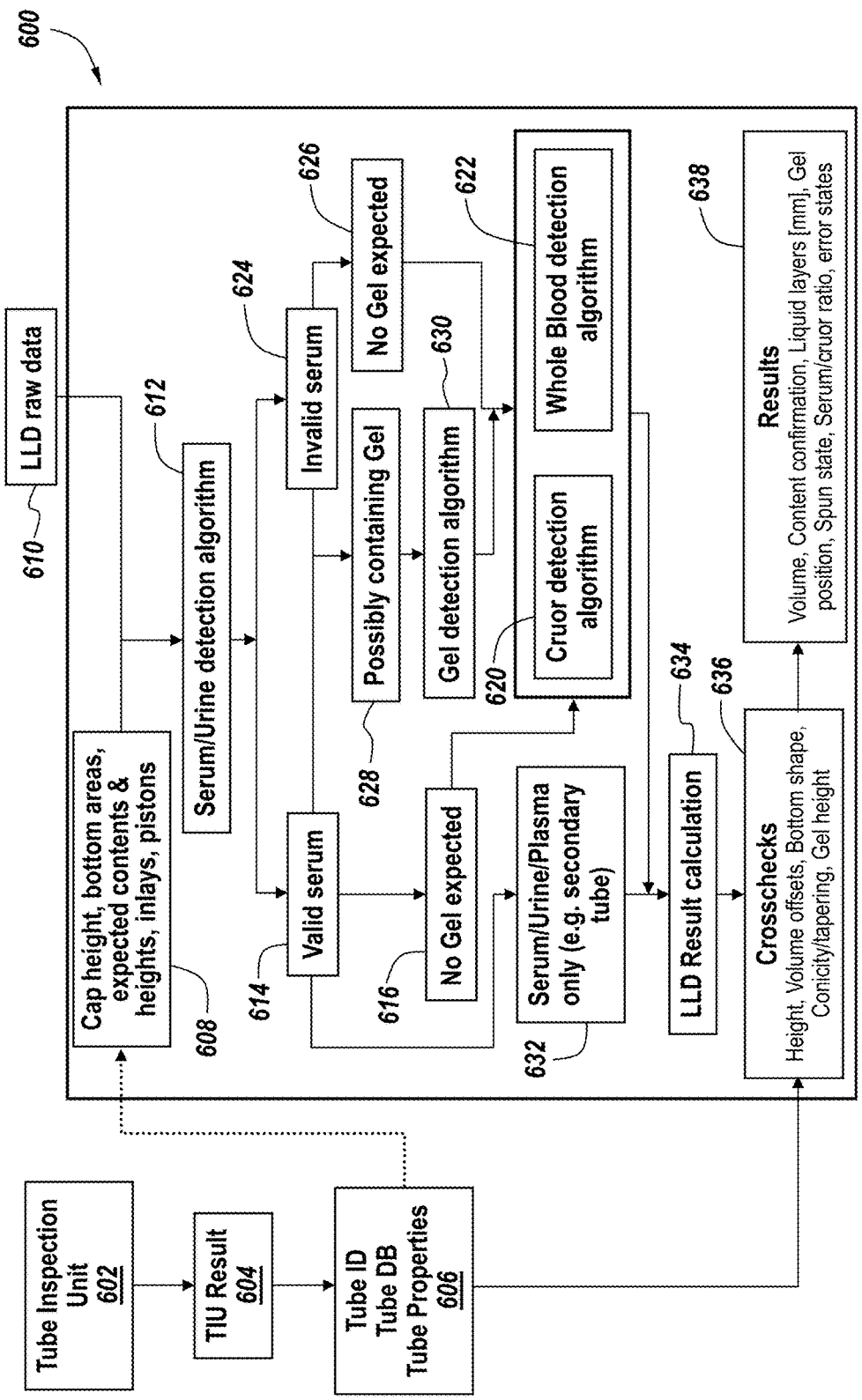
FIG. 6 illustrates an LLD detection process in one embodiment of the invention.

FIG. 6 illustrates a process flow for LLD detection, in one embodiment of the invention.

As illustrated in the figure, a process flow 600 may start with receiving TIU results (604) from a tube inspection unit (602). For example, the TIU measurement unit 112D may perform measurements of a sample container and may provide imager data that may be used to generate the container identification data. The TIU 112 may inspect the container and identify a container type, a cap type and the cap color based on the tube database and tube properties (606). The container identification data may be provided to LLD 114. In parallel or at a different time, LLD raw data may be obtained from the LLD 114. The LLD raw data may include a height measurement of the container (capped or open) and of the content layers.

Data related to certain properties associated with the container such as a cap height, bottom areas, expected contents and heights, inlays and pistons may be provided to the LLD 114. Some of the properties may be used to exclude certain areas in calculation of the content layers. For example, the cap height area may be excluded given the start and end dimensions of the tube as measured by the LLD raw data. Similarly, areas associated with the bottom areas (e.g., false bottom), inlays, pistons, etc. may be excluded from the liquid level calculation since these areas may not contain any liquid. Properties such as expected contents and heights may be determined from the sample type and/or "contains gel" and/or "expected gel height" properties attached to the container (e.g., as stored in the tube database).

The serum/urine detection algorithm (612) may receive the cap height, bottom areas, expected contents and heights, inlays and pistons from the TIU output module 302C (608). The serum/urine detection algorithm 612 may also receive LLD raw data (610). For example, the LLD raw data may be measured by the LLD raw measurement unit 114D. The serum/urine detection algorithm 612 may determine if the serum is a valid or an invalid serum. For example, serum characteristics may be visible in certain wavelengths with reference to FIG. 5. The serum may be valid if the presence of serum is detected and the height of the serum indicates that the serum amount may be sufficient for the analysis (e.g., if more than 4 mm). In some embodiments, the serum may be determined to be invalid based on the water absorption characteristics of the sample (e.g., not enough absorption). The serum/urine detection algorithm may be part of the detection algorithms module 304C.

If the serum is valid (614), and if no gel is expected (616), a cruor detection algorithm may be executed (620) and/or a whole blood detection algorithm may be executed (622). For example, the cruor detection algorithm and the whole blood detection algorithm may be part of the detection algorithms module 304C. The detection algorithms module 304C may utilize the information related to the container identification data provided by the TIU 112 to determine if the sample contains gel or not.

If the serum is invalid (624), and possibly gel is contained, a gel detection algorithm may be executed (630) followed by execution of the cruor detection algorithm (620) and/or the whole blood detection algorithm (622). For example, the gel detection algorithm may be part of the detection algorithms module 304C. If the serum is invalid (624), and no gel is expected (626) based on the container identification data, then the cruor detection algorithm may be executed (620) and/or the whole bold detection algorithm may be executed (622). Next the LLD result calculations may be performed (634). For example, LLD results module 304D may provide a level detection result. In some embodiments, the LLD results module 304D may provide the content layers that are represented in millimeters or any other suitable units.

Note that FIG. 6 illustrates an exemplary process flow that incorporates the detection algorithms in certain sequences. However, the algorithms may be used in any suitable combination or order. In some embodiments, order of the detection algorithms may depend upon the wavelengths used by the LLD 114 (as discussed with reference to FIG. 5) or the measurement apparatus.

If the serum is valid, and is only serum/urine/plasma (e.g., secondary tube), no detection algorithms may be executed (632) and the LLD result calculations may be performed (634). For example, a determination that the container is a secondary tube may be made based on the container/cap type (e.g. no cap). The secondary tubes may only contain serum, urine or plasma without any layers of gel or cruor. Therefore, the detection of gel or a cruor layer may not be needed.

Based on the additional data provided by the TIU 112 and LLD result, cross checks may be performed (636). In some embodiments, the cross checking module 304E may perform cross check on the container identification data and the liquid level detection data. For example, the cross check may be performed based on some of the properties associated with the container such as a height, volume offsets, a bottom shape, a conicity/tapering, gel height, etc.

Results of the cross check may be generated after the cross check is performed (638). In some embodiments, the output module 304F may generate the combined result. For example, the combined result may include a volume, content confirmation, liquid layers, a gel position, a spun state, a serum/cruor ratio and error states. The combined result may be used to plan the route for the sample as discussed with reference to FIG. 10.

Figure 10:
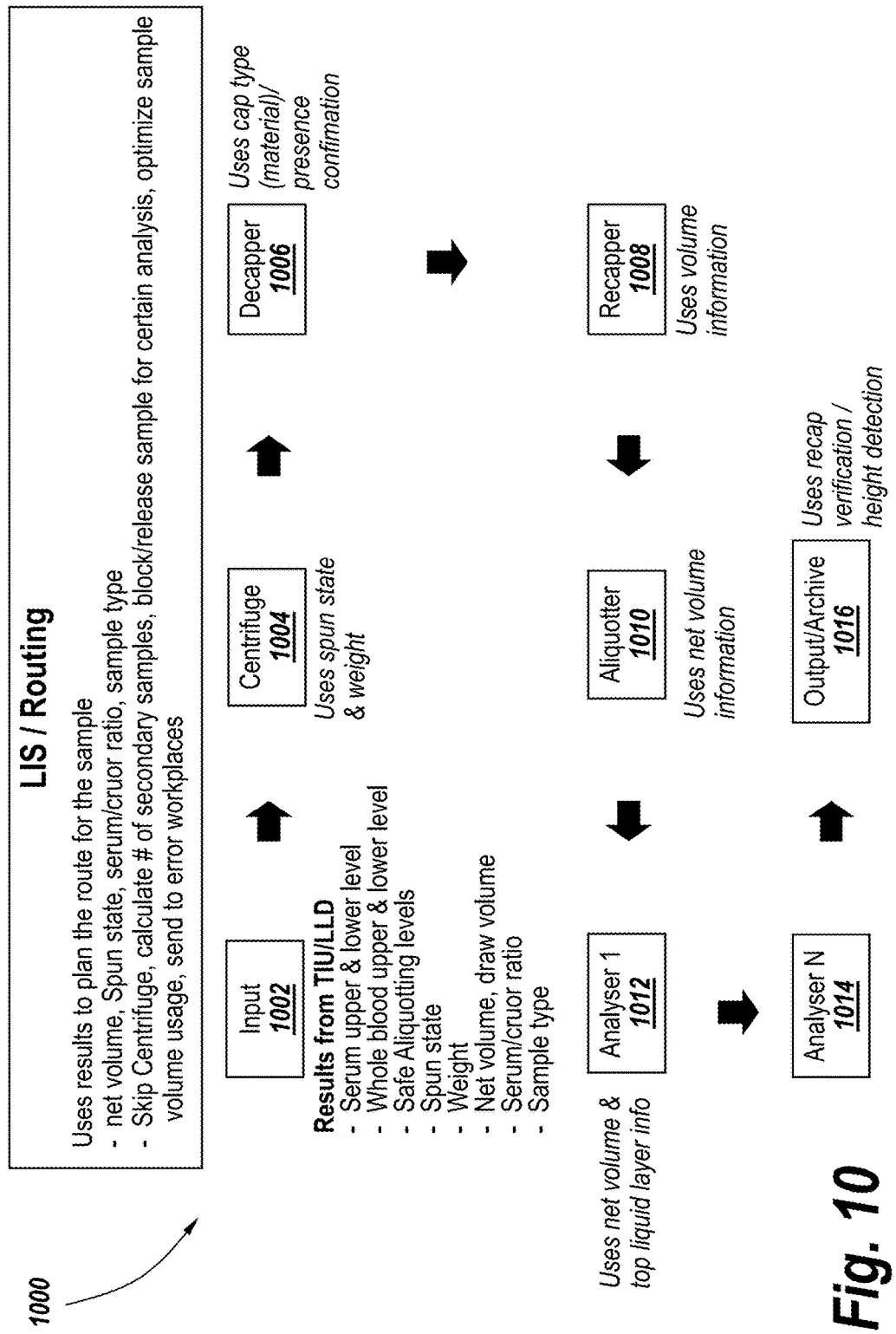
FIG. 10 illustrates a lab workflow using the TIU/LLD combined results, in one embodiment of the invention.

FIG. 10 illustrates a workflow 1000 in the laboratory automation system 100 using the TIU/LLD combined results in one embodiment of the invention. In FIG. 10, "LIS" refers to a laboratory information system. Embodiments of the invention can use the results from TIU and LLD data to route a sample through a laboratory automation system. For example, as explained above, the net volume, spun state, serum/cruor ratio, and sample type may be determined using the TIU and LLD data, and they may be used to determine a proper route for a sample in a laboratory automation system. The LLD and TIU data may also be used to determine whether a sample should skip a centrifuge, calculate a number of secondary samples that are to be derived from a primary sample, determine whether release a sample for certain types of analyses, optimize sample volume usage, and/or determine whether to send the sample to an error workplace.

Embodiments of the invention also have a number of advantages. As noted above, embodiments of the invention can combine TIU and LLD data to provide for a more accurate liquid level determination, thereby improving sample processing. For example, using TIU and LLD data together to calculate a spun state and perform a transition edge verification process can improve the aliquoting process. For example, when the transition between two separated liquid components in a sample tube is accurate, the correct amount of liquid can be safely aliquoted. Further, TIU and LLD data can be used to accurately determine the critical fill level handling for a sample tube, verify detected layers of materials, calculate sample volumes for tubes with different configurations (e.g., conical tubes), and a usable net sample volume using a transition score or confidence threshold. This can also result in improved aliquoting since the correct amount of sample at any given level within a sample tube is known. Further, TIU and LLD data can be used to calculate a spun state and determine critical fill level handling. As explained above, this can result in improved/sample-specific transporting/handling algorithms.

In some embodiments of the invention, results from the TIU/LLD, after the cross check has been performed, may be used to plan a route for the sample container. For example, based on the combined results from the TIU 112 and LLD 144 (e.g., a net volume, a spun state, a serum/cruor ratio, a sample type, etc.) the central controller 102—a) can determine whether the centrifuge can be skipped, b) can calculate the number of secondary samples needed, c) can block/release sample for certain analysis, d) can optimize sample volume usage, e) can send to error workplaces, etc. Note that FIG. 10 illustrates an exemplary workflow for the sample container. However, it will be understood that the results from the TIU/LLD may be used by various components of the laboratory automation system 100 in any order and capacity.

In step 1002, results for a sample container may be obtained from the TIU/LLD. For example, the results may include a serum upper and lower level, a whole blood upper and lower level, safe aliquoting levels, a spun state, a weight, a net volume and a draw volume, a serum/cruor ratio, and a sample type. Referring back to FIG. 6, the results (638) may be provided by the LLD 114 after cross checking (636) the LLD result calculation (634) with the results provided by the TIU (606).

In step 1004, information related to the spun state and the weight of the sample container may be used in centrifuging. Referring back to FIG. 1, the LLD 114 may provide the information related to the spun state and the weight of the same container to the centrifuge unit 116. As discussed previously, this information may be used to detect container breaks in the centrifuge unit 116.

In step 1006, information related to the cap (e.g., cap type, cap material, and confirmation of cap presence) may be used by the decapper. Referring back to FIG. 1, the decapper/recapper unit 118 may utilize the cap type information to determine if the cap is present and if the cap needs to be removed. If the cap needs to be removed, the decapper/recapper unit 118 may remove the cap based on the cap type and material, as the grip force and grip position values may depend on the cap material and its inner structure. In some embodiments, the decapper/recapper unit 118 may use the adjusted decapping profile to avoid spills and contamination during decapping.

In step 1008, information related to the volume (e.g., net volume and/or the draw volume) of the sample container may be used by the recapper. Referring back to FIG. 1, the recapper in the decapper/recapper unit 118 may utilize the volume information for attaching cap to the sample container. In some embodiments, the recapper may reject the recapping request, depending on the type of recapping (e.g., screw cap, push cap, etc.).

In step 1010, information related to the net volume of the sample container may be used by the aliquoter. Referring back to FIG. 1, the aliquoter unit 120 may utilize the net volume information to calculate the number of secondary samples for dividing the contents of the sample container.

In steps 1012 and 1014, information related to the net volume and the top liquid layer of the sample container may be used by one or more analyzers. Referring back to FIG. 1, one or more analyzers in the analyzer unit 122 may utilize the top liquid layer information and net volume information to determine a safety distance and for critical fill level handling.

In step 1016, information related to the recap verification and the height detection of the sample container may be used by an output/archive unit. Referring back to FIG. 1, the output unit 124 may utilize the recap verification information before archiving or storing the sample container.

Embodiments of the invention may be used in the laboratory automation systems, tube identification units, patient sample sorter/handling devices, routing, tube handling algorithms, etc. For example, the TIU 112 and LLD 114 may be used in an input tube robot or centrifuge tube robot of some existing laboratory automation systems (e.g., AutoMate™ 2500 series). In some embodiments, the TIU/LLD results may be used before aliquoting to verify the transition between serum/plasma to the layer below (e.g., cruor/gel). In some embodiments, the TIU/LLD results may be used to calculate available volume including safety offsets. In some embodiments, the TIU/LLD results may be used to provide serum/cruor relation and gel layer position to determine the spun state (e.g., possible states: spun, potentially spun, unspun). In some embodiments, the TIU/LLD results may be used in pre-analytical processing in the laboratory automation systems. For example, when sample data/patient data is entered into laboratory system (e.g., after picking a sample up from the input area and acquiring TIU and LLD data but be/fore the sample is sent to a specific route/pre-analysis task; i.e. while the sample is sitting in the distribution buffer), specific content state detection can influence workflow decisions (e.g. skip centrifuge or spin, process manually, etc.). In some embodiments, the TIU/LLD results may be used in analytical processing such as measuring aspirated volume of analyzers (e.g., when a sample tube is measured by an additional LLD device after sample volume has been drawn from the tube by an analyzer probe).

Liquid Level Detection with Multi-Angle Measurements

Figure 12:
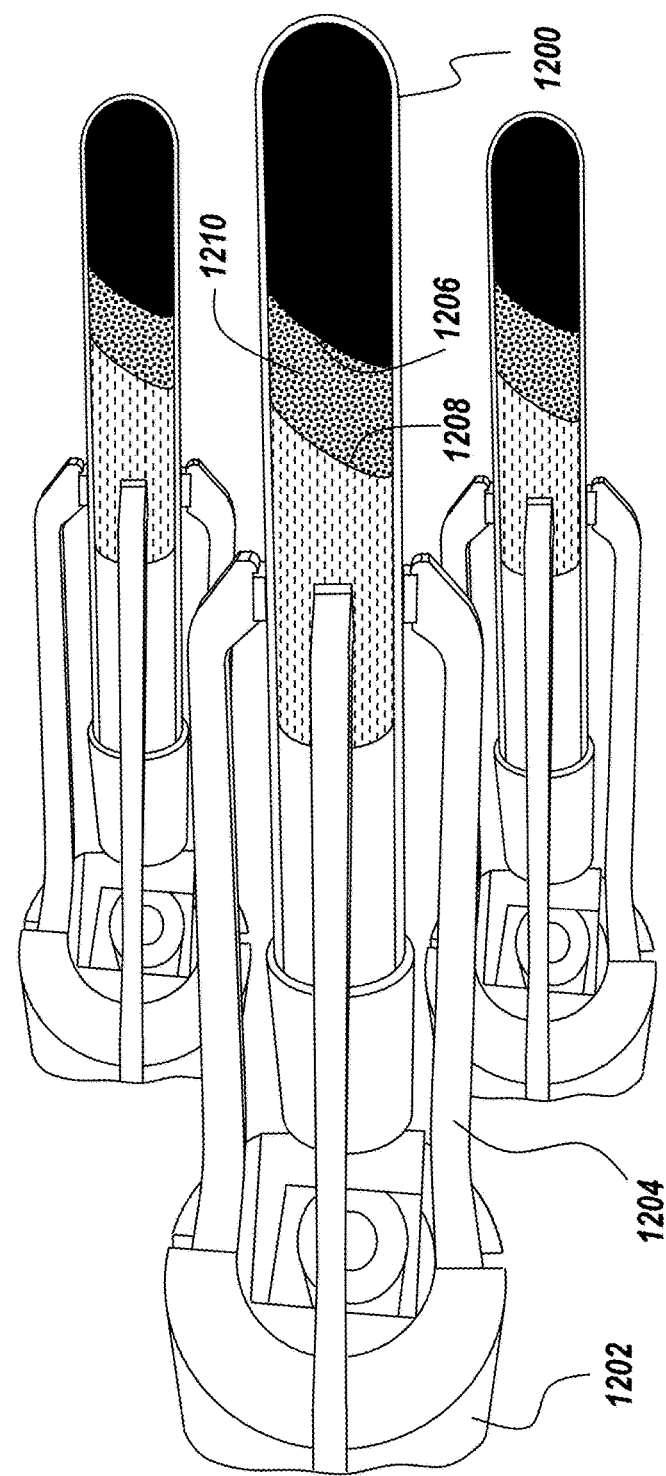
FIG. 12 illustrates an exemplary sample tube holding tilted sample, in one embodiment of the invention.

The liquid level detection (LLD) unit 114 illustrated in FIGS. 2 and 3B may measure the light signal that passes through the sample tube containing a sample at a single angle that is chosen randomly. That is, the light signal may pass through a single portion of the tube. Detecting liquid levels by measuring the light signal that passes through the sample tube at a single angle (i.e. directing the light to a single portion of the tube) assumes that all the liquid levels are perpendicular to the tube wall and that the sample tube is held vertically. However, there may be cases where the liquid levels are not perpendicular to the tube wall and/or the sample tube is not held vertically by, for example, the robotic arm. FIG. 12 illustrates a sample tube 1200 held by a robotic arm 1202 having one or more prongs 1204. As illustrated in FIG. 12, the lower interface 1206 and the upper interface 1208 of the gel portion 1210 are tilted significantly.

Figure 13:
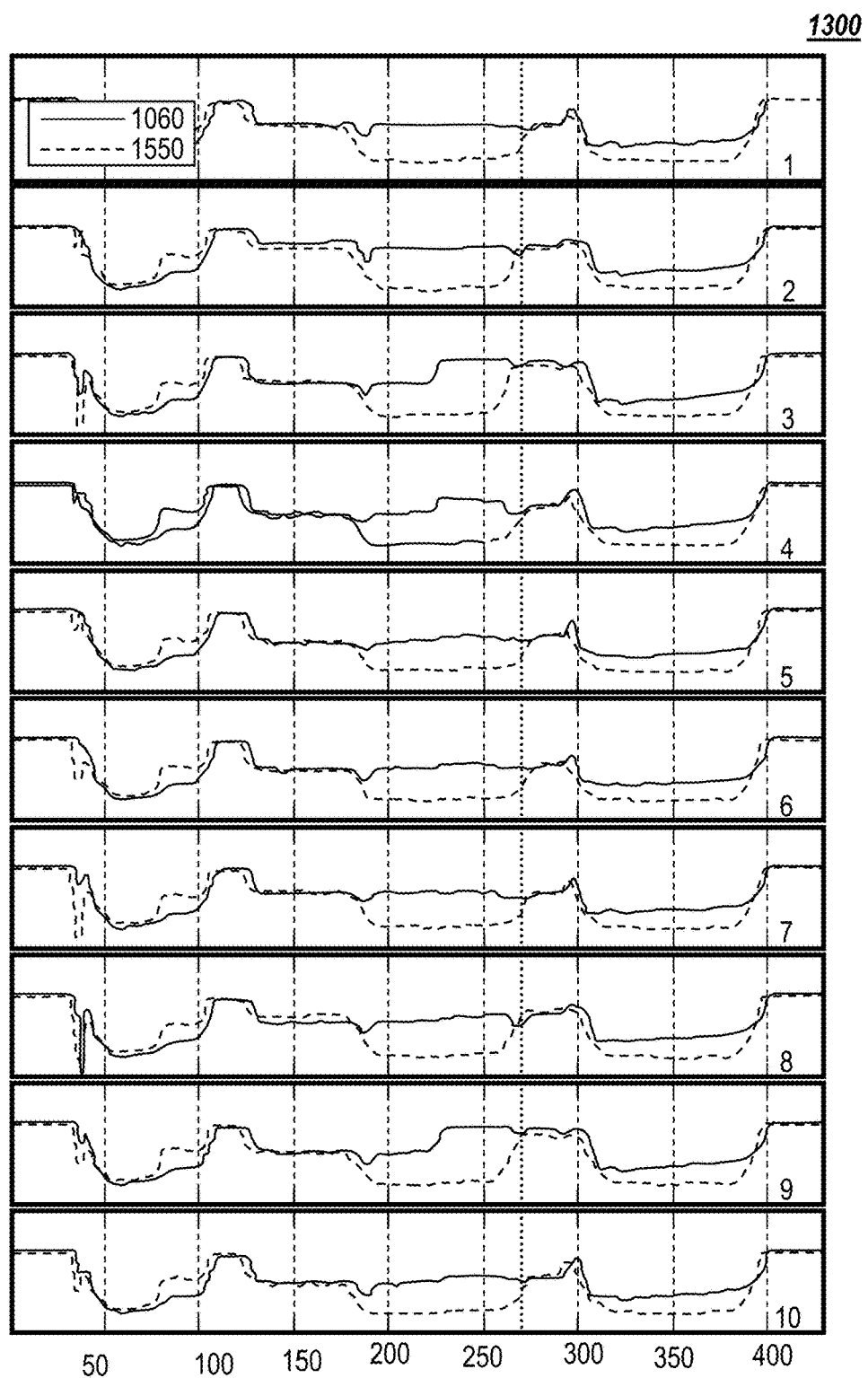
FIG. 13 illustrates the results of an experiment where the LLD signal measurement is carried out n=10 times for a given sample tube, in one embodiment of the invention.

FIG. 13 illustrates the results 1300 of an experiment where the LLD signal measurement is carried out n=10 times for a tilted sample provided in a sample tube. The sample tube is rotated around z-axis by 360° *(i−1)/n for the i-th signal measurement. Therefore, the signal measurements are uniformly distributed in 360°. Each graph corresponds to a single angle measurement with a 1060 nm and a 1550 nm wavelength of Infra-Red (IR) light. Specifically, the transmission property of the 1060 nm and 1550 nm wavelengths through a water sample varies from one another considerably. Thus, using such a combination of wavelengths with said different transmission properties, e.g. 1060 nm and 1550 nm, it is possible to identify the serum portion (e.g. water like portion) of the sample. For example, in the exemplary plots illustrated in FIG. 13, the serum is identified between index numbers 180 and 260. Once the serum portion is identified, the serum-gel transition and the gel portions may be identified as segments adjacent to the serum. For example, in the exemplary graphs illustrated in FIG. 13, the serum-gel transition is provided at index numbers 260-270 (i.e. on the right side of the serum portion) and the gel is provided at index numbers 270-300 (i.e. on the right side of the serum-gel transition portion).

FIG. 13 illustrates a collection of 10 sets of data measured on the same sample tube at 10 different angles. It is observed that there are substantial variations of serum-gel and gel-cruor transitions with respect to rotating angle, i.e. there are substantial variations among each individual measurement. This implies that for tilted liquid levels, measuring signal at a single rotating angle will result in intrinsically inaccurate result.

According to various embodiments, liquid levels in a sample tube may be detected at multiple portions of the tube corresponding, for example, to multiple measurement angles. In some embodiments, the sample tube may be rotated by a predefined angle between two consecutive measurements. In other embodiments, multiple pairs of light source and light detector may be provided around the sample tube for taking multiple measurements simultaneously. Yet in other embodiments, the sample tube may be rotated while moving up or down, which will result in a spiral scanning path. Alternatively, the pair of light source and light detector may be rotated around the sample tube.

An exemplary multi-angle measurement process may start with a LLD measurement at rotation 0° which creates the first LLD measurement. TIU may spot the barcode on the sample tube and cause a rotation of the sample tube so that a readable part of the barcode faces the TIU camera. The rotation distance in relation to the LLD can be anywhere from −180° to 0° to +180°. The robotic arm holding the sample tube may prepare the tube rotation for the second LLD measurement in a way for the light detector to measure at a different angle (e.g. sector) than in the first measurement. In embodiments where the gripper robotic arm includes four gripper fingers (e.g. prongs), there may be four sectors, defined by the space between respectively adjacent gripper fingers, where the light beam can enter and pass through the sample tube. If the first sector was used in the first measurement, for the second measurement one of the remaining sectors, i.e. sector two, three or four, may be used. In some embodiments, each sector may be divided into one or more subsectors. One of ordinary skill in the art will appreciate that four sectors discussed herein are provided for illustration purposes only and should not be construed limiting. The measurements subsequent to the first one may be run in the same or other sectors as long as the gripper fingers do not interrupt illumination light and the measurements are not acquired at the same rotational angle. According to various embodiments, measurement results may be different, even if the axis of transmission is the same, dependent on the structure of the material/liquid/gel layers that are passed though by the light. Light scattering may be different, if the light contacts a partially absorbing material layer right after entering the tube as compared to a case, where the light passes through the tube and contacts that layer just before leaving the tube (e.g. in a case of a tilted gel or cruor surface). Accordingly, the measurement value is not only determined by the materials the illumination light passes through but also the order of the materials. That is, the measurement value taken at angle 0° may not be the same as the one taken at angle 180°. According to various embodiments, a best viewing angle may be determined among the multi-angle measurements and used for optimum measurement, which may be equivalent to a curve which would provide the best determinations for the liquid levels.

Figure 14:
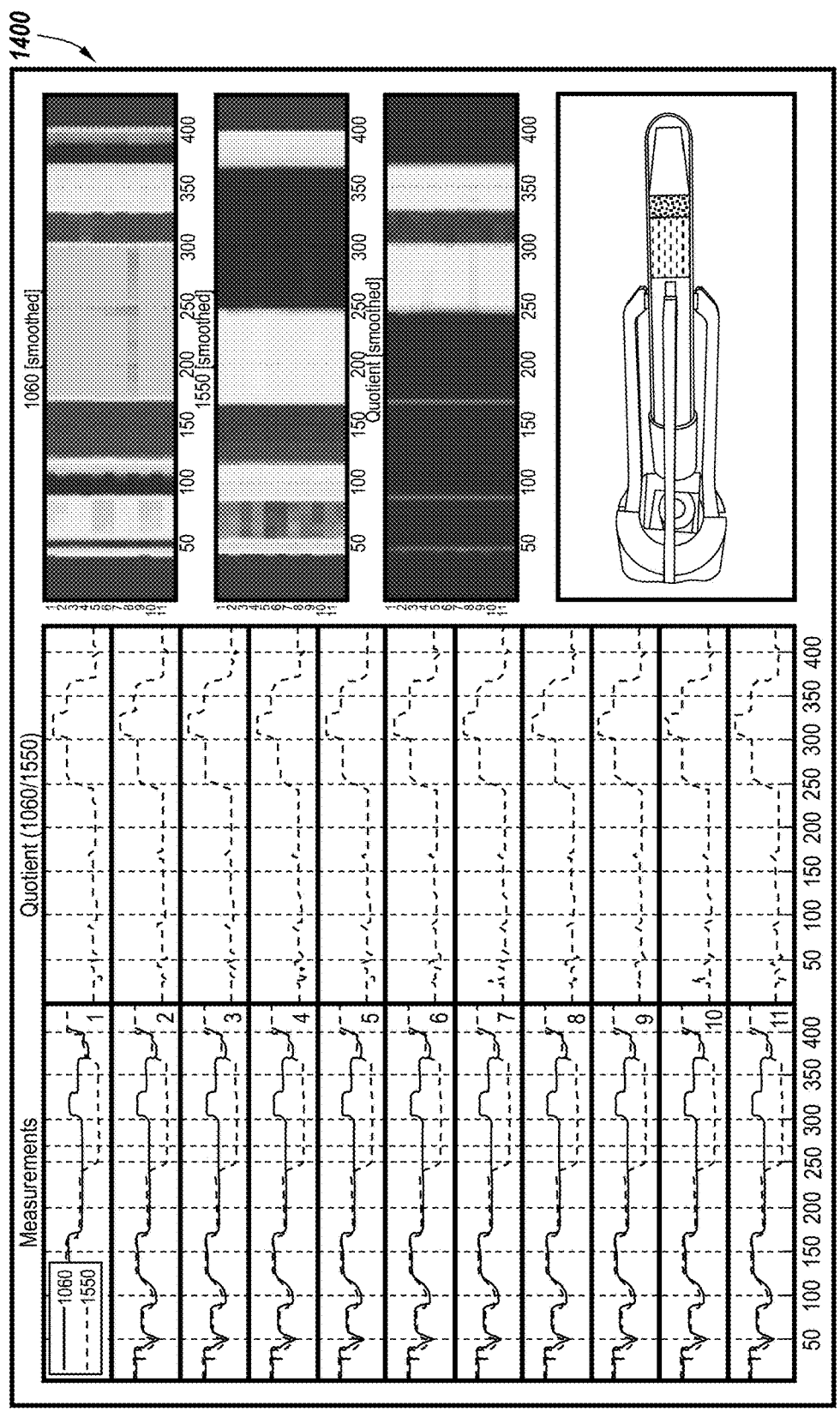
FIG. 14 illustrates a profile map showing multiple angle measurements, in one embodiment of the invention.

Multiple angle measurements may be illustrated using a profile map, such as profile map 1400 illustrated in FIG. 14. The y-axis of the profile map 1400 is an angle index, each index corresponding to a unique angle at which signal is measured. The x-axis of the profile map 1400 indexes the readings of each measurement in terms of index numbers. The shades in the profile maps represents relative quantity of each measurement in its own profile map, e.g., 1060 nm measurement, 1550 nm measurement or their quotient (i.e. the ratio of 1060 nm measurement/1550 nm measurement). The darker the color is, the greater the measurement is. One of ordinary skill in the art will appreciate that any number of profile maps associated with various IR measurements may be used to determine the tube and sample properties. The use of profile maps associated with 1060 nm measurement, 1550 nm measurement or their quotient provided in FIG. 14 is for illustration purposes and should not be construed as limiting.

In a normal condition when all liquid levels are perpendicular to the tube wall and the sample tube is vertical (such as the sample tube 502 illustrated in FIG. 5), one will see perfectly vertical patterns in the profile maps. On the other hand, when the liquid levels in the sample tube are tilted, multi-angle measurements make it possible to detect more structure of the tube and the sample, recognize tilted liquid interface, detect system issues, improve quality of liquid level detection and retrieve information of label position and orientation. Each of these advantages will be discussed next in greater detail.

1. Detect More Structure of the Tube and Sample

When there is only one measurement angle of the tube and the sample, the measurement may be contaminated with noise. Consequently, it may be hard to determine whether a certain feature in the measurements is caused by the structure of the tube (or the sample in the tube) or is a product of the noise generated by the system during data acquisition. In contrast, multi-angle measurements may be used to smooth out the noise and reinforce genuine features in the measurements.

Figure 15:
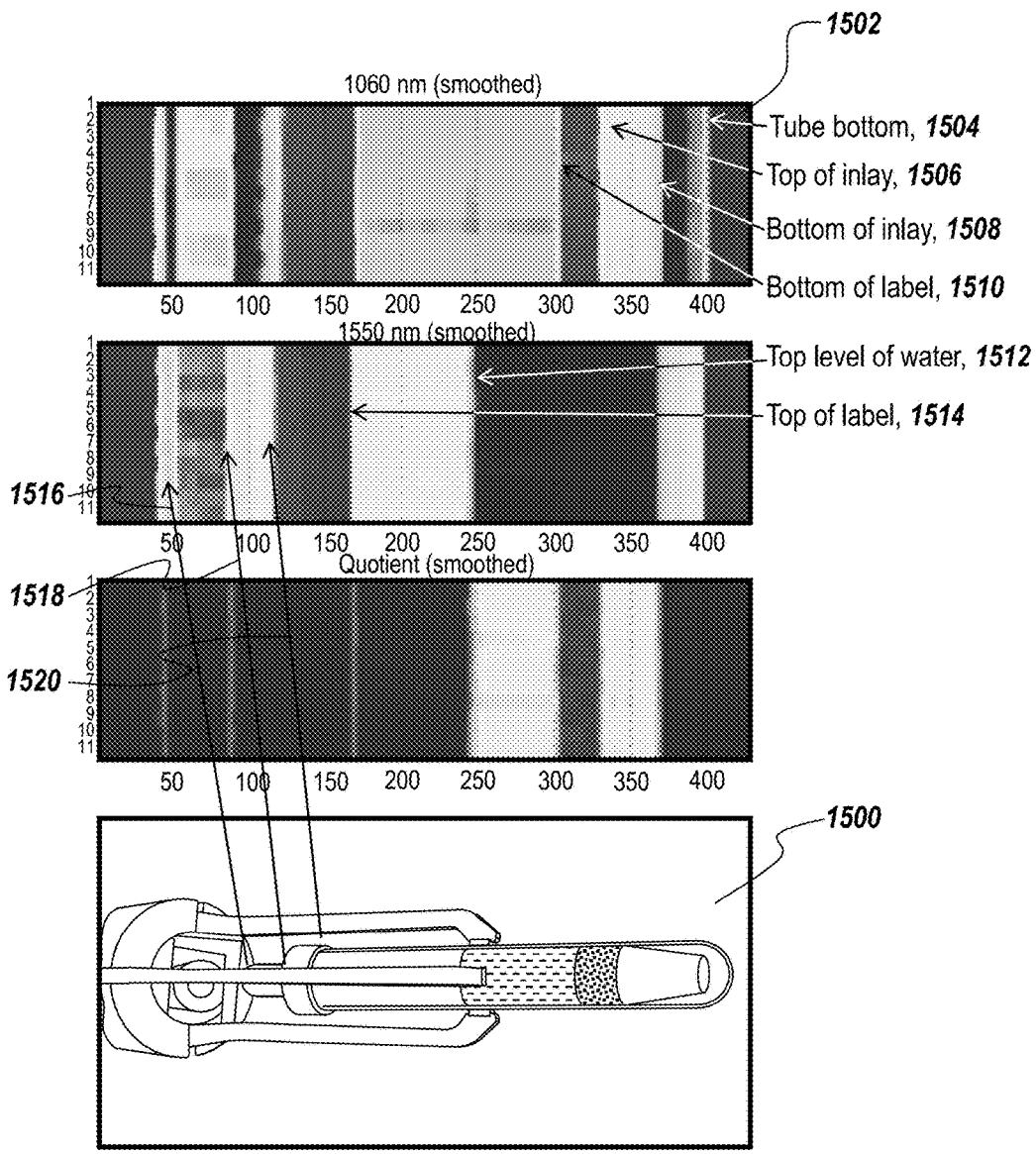
FIG. 15 illustrates an exemplary sample tube containing water sample and the corresponding profile map composed of measurements at multiple angles of the water sample, in one embodiment of the invention.

FIG. 15 illustrates a sample tube containing water 1500 and the corresponding profile map 1502. The profile map 1502 is composed of measurements at multiple angles of the water sample. By stacking multi-angle measurements, it is clear that the vertical lines in the profile map of 1060 nm, 1550 nm, and quotient unveils the structure of liquids, tube, cap, and labels such as the tube bottom 1504, the top of bottom inlay 1506, the bottom of bottom inlay 1508, the bottom of label 1510, the top level of water sample 1512, the top of label 1514, and the cap geometry 1516, 1518, 1520.

The highest measurement with both wavelengths (i.e. 1060 nm and 1550 nm) is obtained when the light passes through air (i.e. the intensity of the light is not reduced by passing through an object or material). The highest measurements are illustrated with dark shades in the profile maps 1502. Accordingly, the dark areas at the beginning and end of the profile map illustrate the area above the tube (i.e. above the cap of the tube) and the area below the tube (i.e. below the bottom of the tube), respectively. Thus, the bottom of the tube 1504 can be identified around index number 400. Around index number 400, the dark shade ends, which indicates the top 1516 of the cap. The top 1516 of the cap is the first object that the light hits (and passes through) after the void/air above the cap. The neck 1518 and the bottom 1520 of the cap may be identified based on the shade changes adjacent to the top 1516 of the cap. The profile map 1502 also illustrates another dark area around index number 150. As provided above, the dark areas correspond to the IR waves passing through air. Thus, the area around index number 150 corresponds to the air in the tube, below the bottom 1520 of the cap and above the label 1514.

According to various embodiments, image processing techniques (e.g. image segmentation, edge detection, filtering and the like) may be used directly on the 2D profile map to identify the structure of the sample tube and its contents. Alternatively, multi-angle measurement may be fused into a single measurement using techniques such as signal alignment, shifting compensation, averaging, weighted averaging, filtering across multiple angles and the like. The resulting 1D output may have less noise and variations in the fused measurements and represent more genuine tube and sample structure.

With multi-angle measurements, 3D structure of the tube, the sample, the cap and/or the label may also be reconstructed. The reconstructed 3D structure may have rich information about each of the sample, tube, cap, and/or label. The information may improve the outputs that are produced by the LLD unit and also generate new outputs either for system operation or clinical usage. Since the 3D reconstruction is based on light transmission, it can unveil internal structure of the tube or the sample, which may not be seen with reflection of visible light.

2. Handing Tilted Liquid Interface

Figure 16A:
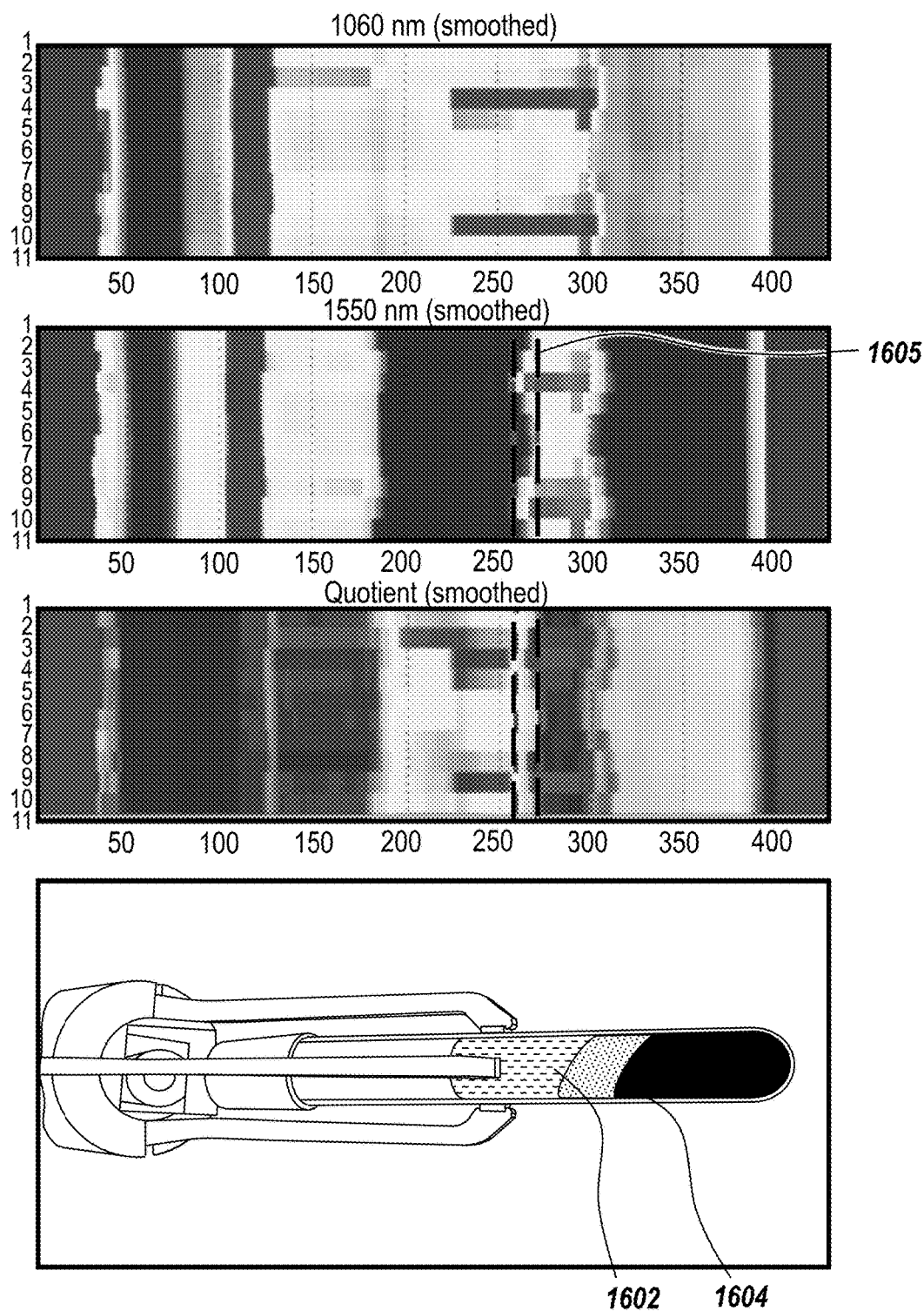
FIG. 16A illustrates an exemplary sample tube containing a tilted serum-gel interface and a tilted gel-cruor interface, in one embodiment of the invention.

As provided above, the liquid levels in a sample tube may not always be perpendicular to the light path. For example, this may be caused by tilted gel and/or tilted cruor. When this happens, a single measurement value may not be enough to identify a tilted liquid level. FIG. 16A illustrates an example of tilted serum-gel interface 1602 and gel-cruor interface 1604. An observed bottom level of serum with a single measurement angle can be anywhere between the two dashed lines 1606. If the system is working with a single angle measurement, the data for the bottom level of serum will be determined based on a single line (e.g. a single index from 1 to 10 on the y-axis). As shown in FIG. 16A, the values change from one index to the next around index number 270. Specifically, the distance between the two dashed lines 1606 may be an indicator of the error that may result in the liquid level detection and volume calculation. In FIG. 16A, the distance between the two dashed lines 1606 range around 3-5 mm. This corresponds to a vertical position offset of the respective measurement positions of the measured sample tube. For example, given a sample tube with inner diameter of 10-16 mm, a 3-5 mm error in liquid height will result in 235 μl-1 ml error in liquid volume, whereas the customer acceptance may be below 250 μl.

Figure 16B:
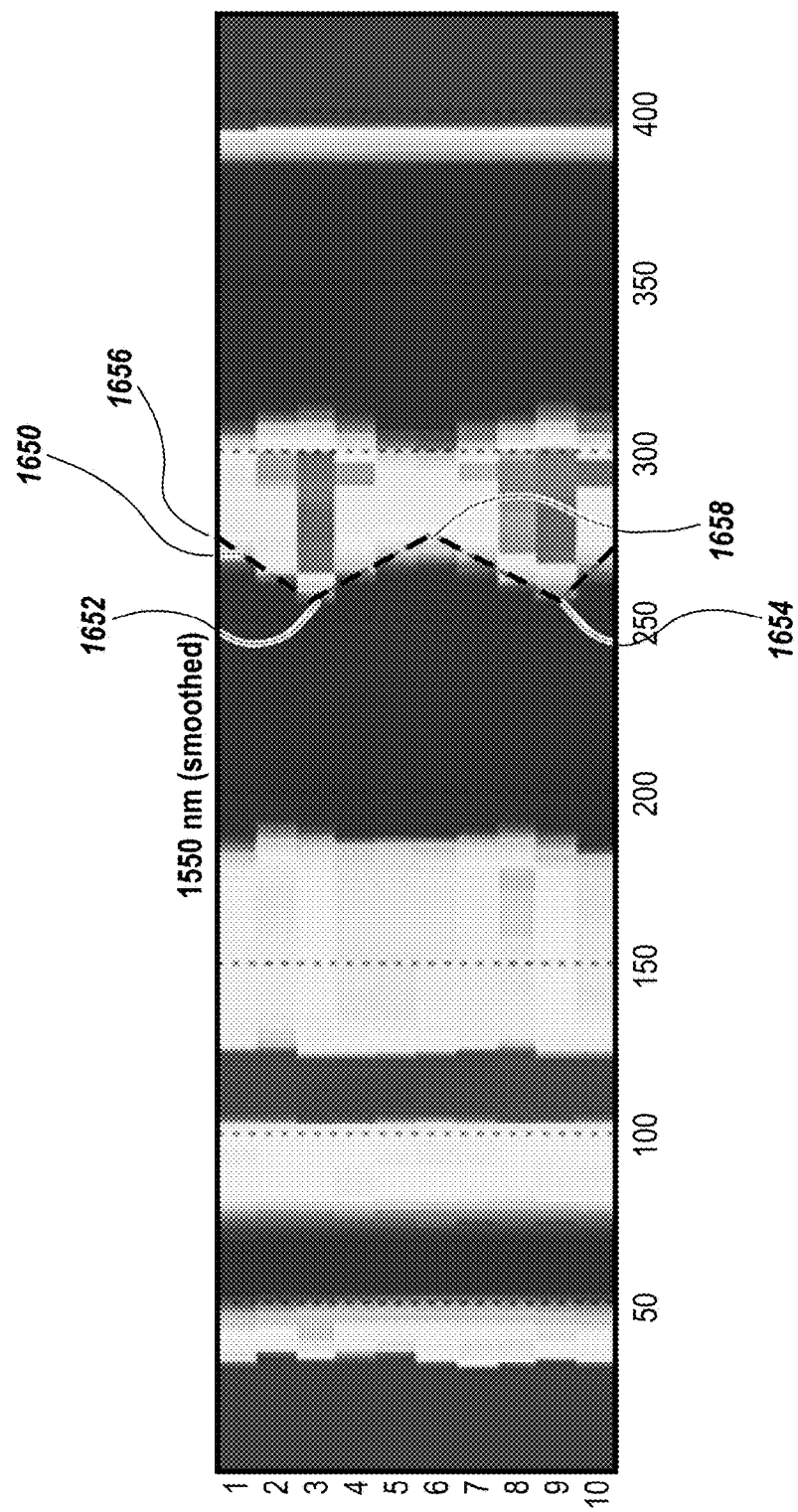
FIG. 16B illustrates a simple linear slope representing the tilted liquid interfaces of FIG. 16A using multi-angle measurements, in one embodiment of the invention.

Using multi-angle measurements (e.g. measuring light transition at multiple angles), the shape of the tilted liquid interfaces may be determined. FIG. 16B illustrates the 1550 nm profile map illustrated in FIG. 16A. However, using the multi-angle measurement data points (i.e. all lines corresponding to indexes 1 to 10 on the y-axis), the tilted interface can be detected as a simple linear slope 1650. The depth of the tilted interface may be estimated based on the steepness of the slope 1650. The $3^{rd}$ measurement 1652 and the $9^{th}$ measurement 1654 indicate the top of the tilted serum-gel interface. The $1^{st}$ measurement 1656 and the $6^{th}$ measurement 1658 indicate the bottom of the tilted serum-gel interface. If the tilted interface is not a simple slope, more complicated formula may be used to describe the shape of the tilted interface. The estimated shape of liquid interface may improve volume calculation, and provide more information to other components of the automation system to make better decisions.

3. Detection of System Issues

Figure 17A:
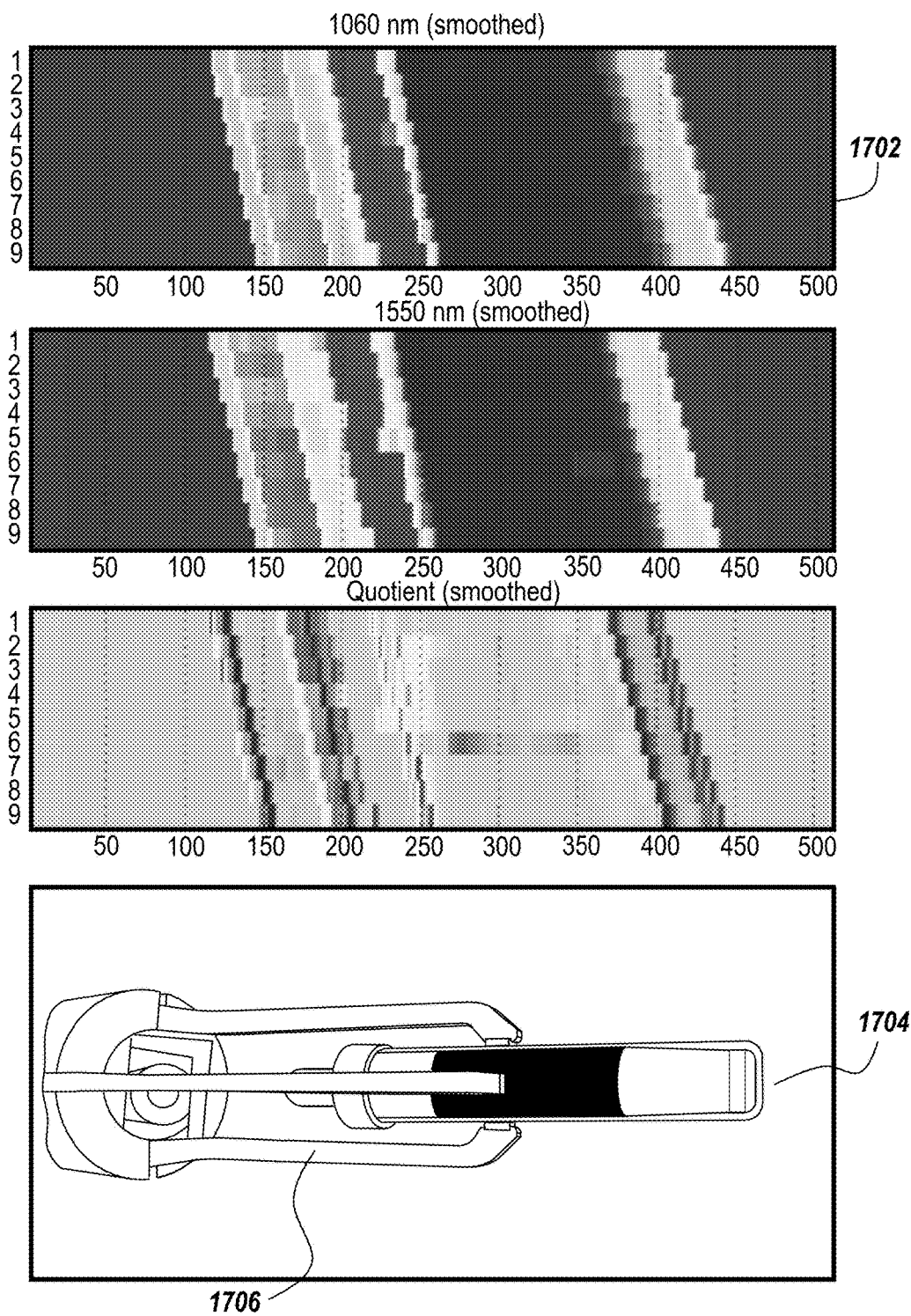
FIG. 17A illustrates a profile map depicting a signal shift across measurement angle, there is signal shift, in one embodiment of the invention.
Figure 17B:
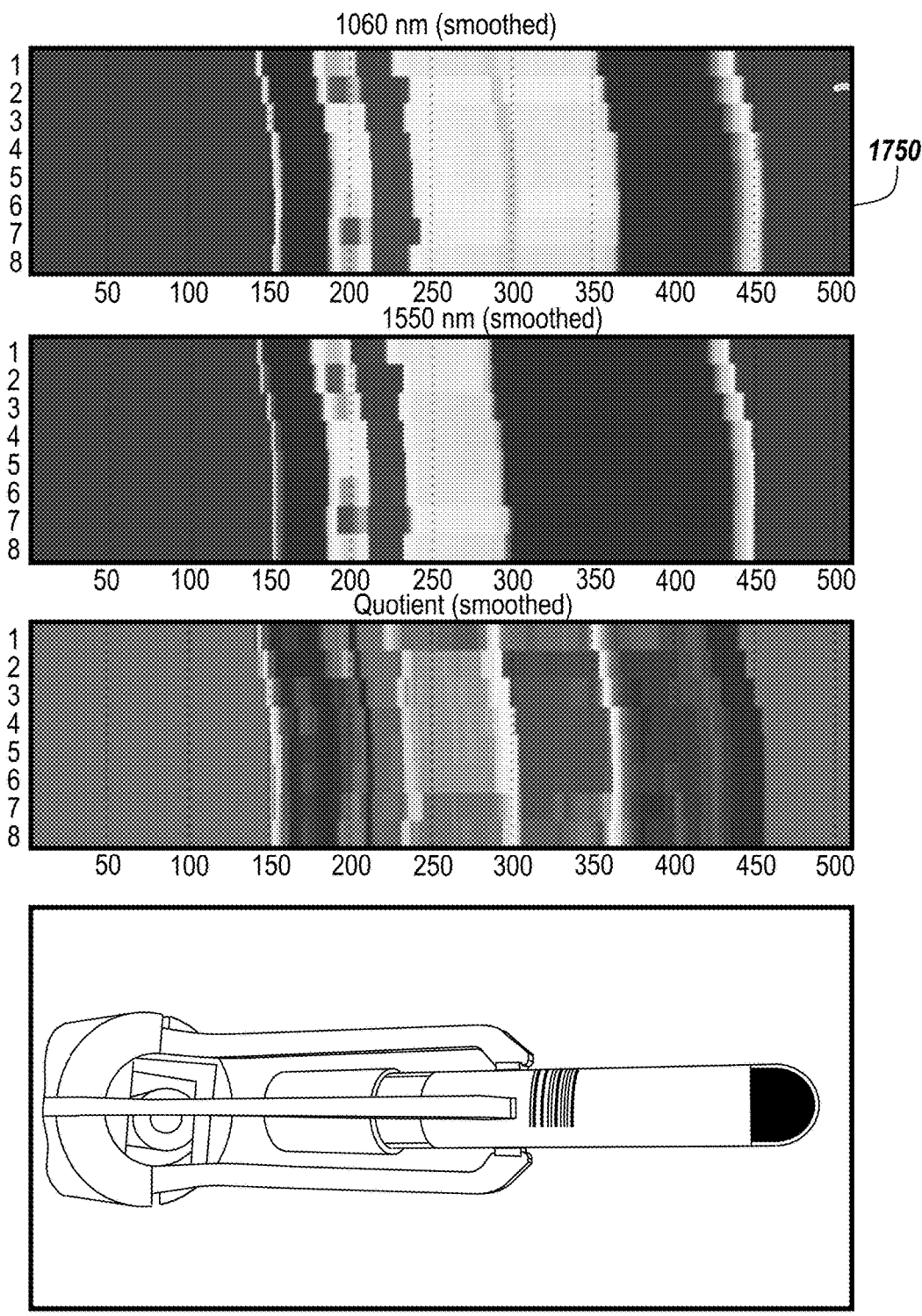
FIG. 17B illustrates profile map depicting a signal shift at some measurement angles but not all, in one embodiment of the invention.

Various system issues that cannot be detected with single-angle measurement may be detected using multi-angle measurements. For example, the profile map 1702 illustrated in FIG. 17A depicts a signal shift across measurement angle. In the exemplary measurement illustrated in FIG. 17A, the sample tube 1704 may have slipped down in the robotic arm 1706 when the system was taking the measurements. Similarly, FIG. 17B illustrates a profile map 1750 with signal shift at some measurement angles but not all. Both FIGS. 17A and 17B manifest a kind of system issue such as dirty measurement lens, problem with light source, problem with robotic arm, etc. that distort the light when the system is collecting a reading. Situations like those illustrated in FIGS. 17A-17B may be detected by comparing counterpart characteristics across all measurement angles. A system alert may be set for early warning and/or monitoring.

According to various embodiments, multi-angle measurements may be used to detect a tilted tube by examining the tube geometry (e.g. features of tube top and bottom) or cap geometry (e.g. feature of cap top) in the profile map.

4. Improve Quality of Liquid Level Detection

Figure 18:
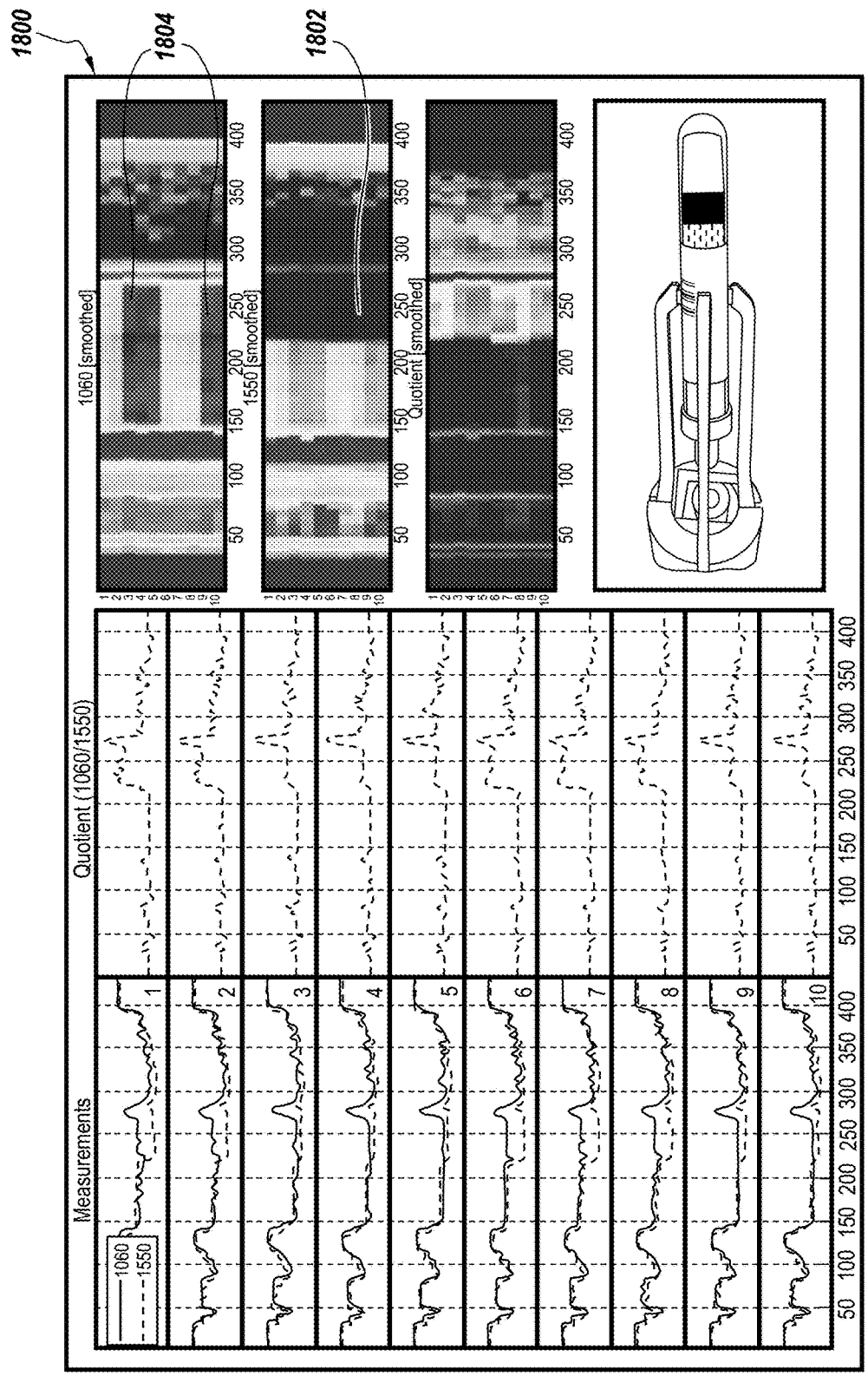
FIG. 18 illustrates a profile map for multi-angle measurements where the water-like feature of serum is very weak at certain measurement angles, in one embodiment of the invention.

Single-angle-based LLD algorithms may suffer from interference. FIG. 18 illustrates a profile map 1800 for multi-angle measurements where the water-like feature of serum is very weak at $3^{th}$, $4^{th}$, $5^{th}$, $9^{th}$, and $10^{th}$ measurement angles, as illustrated by the dark horizontal lines 1804 between index numbers 150 and 270. The 1060 nm signal is slightly stronger than the 1550 nm signal, which makes the LLD algorithm struggle to determine whether the signals between 220 and 270 (the vertical dark area 1802 around index number 250) are from the serum or not. The probability that the LLD algorithm makes a wrong determination increases due to the weak pattern. The multi-angle measurements provide a big picture of the tube and the sample and it is easy to tell that the weak features around 220 and 270 at $3^{th}$, $4^{th}$, $5^{th}$, $9^{th}$, and $10^{th}$ measurement angle are due to the light having to pass the label twice, the first pass being at measurements 3, 4 and 5 and the second pass being at measurements 9 and 10. Using the multi-angle measurements, especially strong property of the serum between 220 and 270 at $3^{rd}$, $2^{nd}$, $6^{th}$, $7^{th}$, and $8^{th}$ angles, it can be determined that the top serum level is around 220 instead of 270.

5. Retrieve Information of Label Position and Orientation

Figure 19:
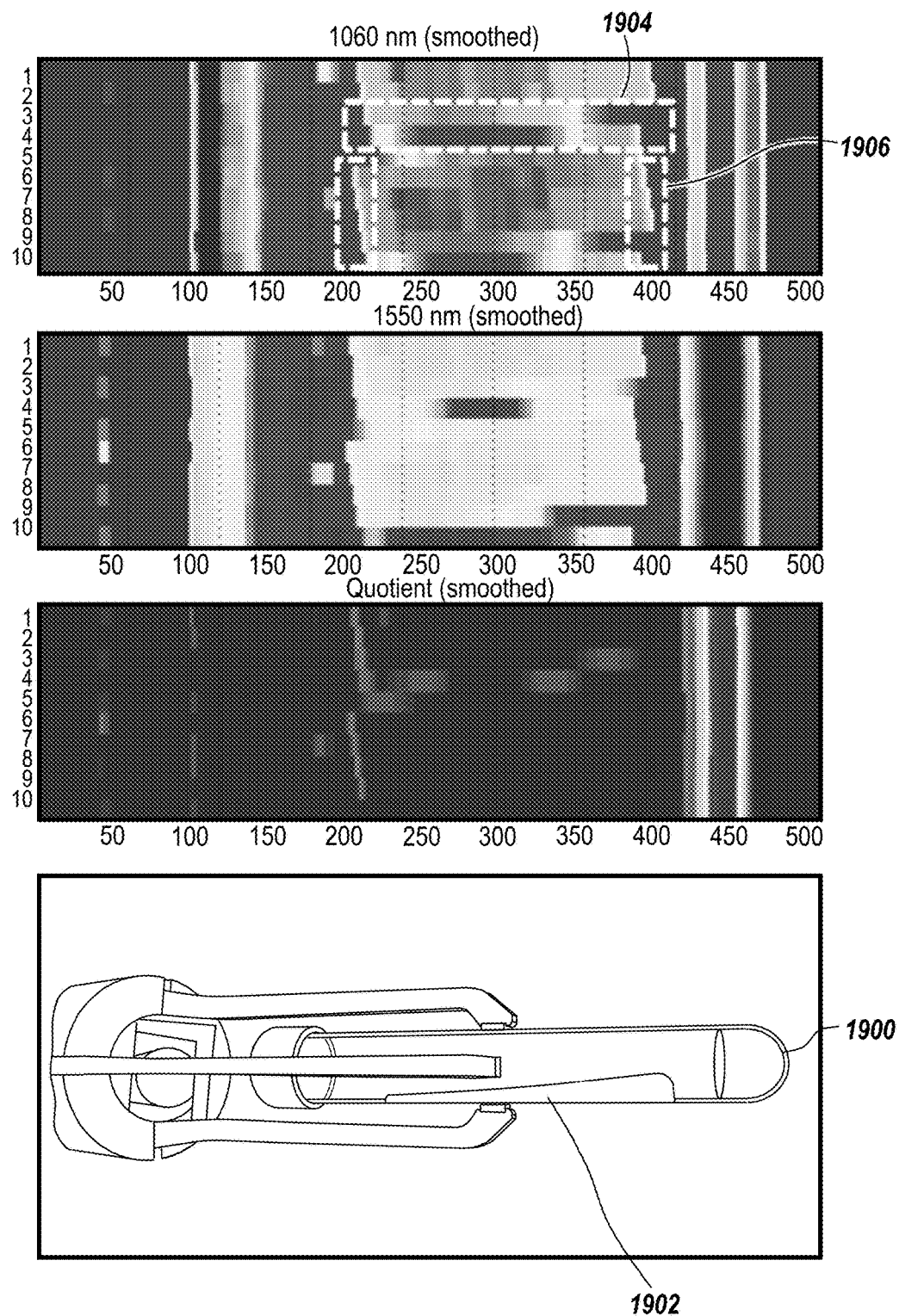
FIG. 19 illustrates an exemplary water sample tube with a tilted label around the tube, in one embodiment of the invention.

The multi-angle measurement can also unveil information about the labels attached around the tube. FIG. 19 illustrates an exemplary water sample tube 1900 with a tilted label 1902 around the tube. The tilted label 1902 exhibits a clear pattern both along the tube wall 1904 and perpendicular to the tube wall 1906 (as illustrated by the dashed boxes), which can be detected by an algorithm. The label may be determined between reading 170 and 340 in the profile map.

Using label structure detection, it can be determined whether liquid levels can be seen from outside, or put in another way, whether there is an optical gap (either from tube top to tube bottom or at the area of interest) on the tube wall, which is not covered by the label. The detection of the optical gap may enable/disable the use of the camera-based device, TIU, which measures reflected visible light, to detect liquid levels. The optical gap does not have to be straight and can be curved with some limitations.

In addition, using label structure detection, image-based (i.e. machine-vision-based) detection of Lipemia, Icterus, and Hemolysis (LIH) or serum indices may be enabled. The common approach of LIH check is invasive, which requires opening the cap. Image-based LIH detection is non-invasive but requires an optical path (e.g. optical gap) that is not obstructed by any labels or obstructed by a single label. Given the multi-angle profile map, it can be determined whether the optical path exists. If there is an optical path, machine vision may be used to detect LIH. The combination of identifying the optical path of no label or a single label, serum layers, and LIH check with machine vision could provide a non-invasive solution, which streamlines the workflow, increase throughput, and improve reliability.

Moreover, using label structure detection, an optimal path can be determined for scanning tube for LLD. Scanning tube to acquire light transmission signal does not necessarily follow a straight line. To minimize the adverse effect of labels, a curved scanning path could be chosen so that the obstruction of labels to laser light is minimum at each tube height altitude. For example, the optimal path may be defined as the one on which 1060 nm signal is maximum at the same tube height altitude on the profile map. Along the optimal path, an optimal measurement can be synthesized and used in the LLD algorithm to minimize the interference from labels.

Transmittance Based Tube Characterization and Classification

Both tube properties (including type, geometry, dimensions, and the like) and liquid level positions are necessary for volume calculation and other processes in an automation system. According to various embodiments discussed above, the calculation of tube properties and liquid levels may be separated and accomplished by two modules, the tube inspection unit (TIU) and the liquid level detection (LLD) module. Tube properties may be detected with a dedicated TIU which is camera based and works independent of LLD while the software run on LLD module may extract sample level positions from the light transmission measurements.

According to various embodiments discussed below, the light transmission measurements may also be used to detect tube properties. The tube properties to be measured may include, among other properties, the inner and/or outer tube diameter, the cap height, the inlay depth and types of cap and bottom inlay. With the knowledge of the tube and cap structures, the liquid level positions can be determined more accurately and reliably. The combination of the knowledge of the tube and the liquid levels may enable volume calculation to be accomplished solely using the LLD module. Furthermore, the measured tube properties may be used directly by downstream components and/or be used to crosscheck with the counterparts generated by other modules, such as the TIU.

1. Measurement of Cap Height

Figure 20A:
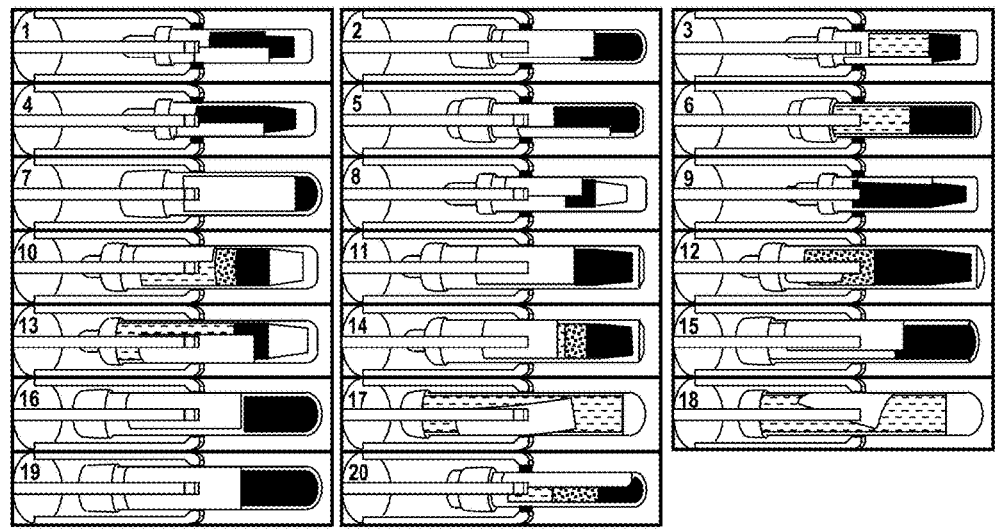
FIG. 20A illustrates a plurality of (e.g. twenty) sample tubes containing samples where the samples tubes have different geometries, caps and sample levels, in one embodiment of the invention.
Figure 20B:
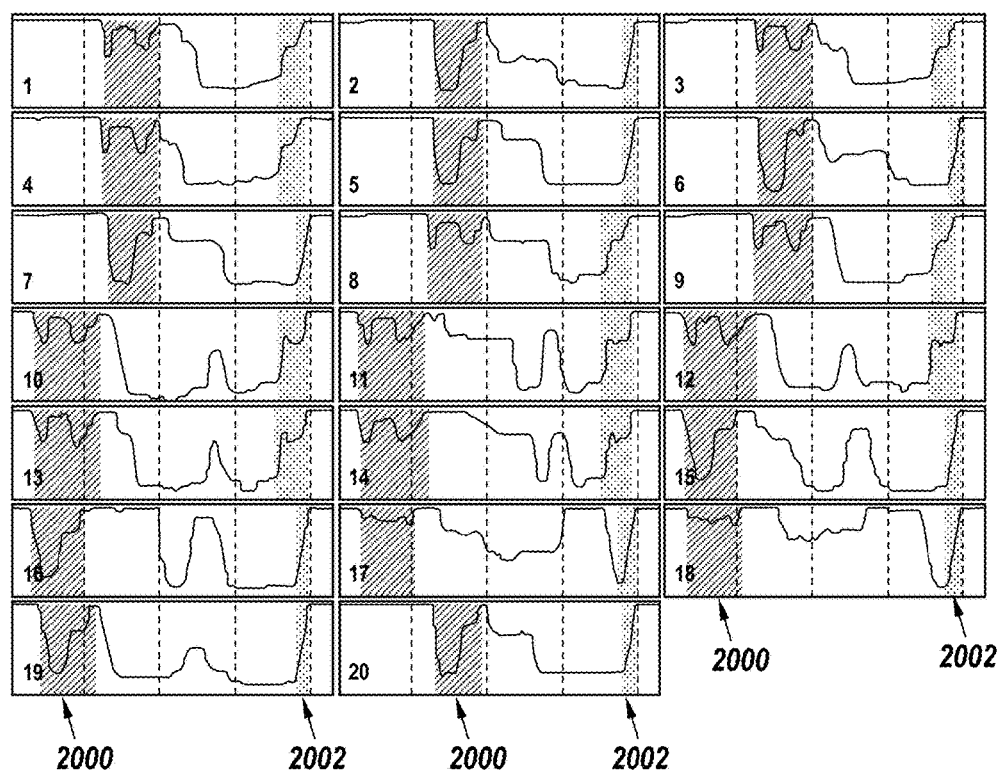
FIG. 20B illustrates the light transmission measurements for each of the tubes illustrated in FIG. 20A, in one embodiment of the invention.

The cap height may be estimated from LLD measurements by locating the upper and the lower edges of the cap. While the cap top may be simply determined by locating the first signal drop on the measurement, identifying the lower edge may be assisted with other position information (e.g. the position of the cap top and the position of the sample top) which is derived in the LLD module. Using the position of the cap top and the position of the sample top, a search area may be delimited and the lower cap edge may be roughly determined by locating the maximum measurement value within the delimited area. The determination may be accomplished due to the unloaded tube section which is below the cap and above the sample solution absorbing less light compared to the cap and the sample solution. Once rough estimation is achieved, the edge position may be refined by determining the rapidest change of signal change (2nd derivative of measurement value) nearby. FIG. 20A illustrates a plurality of (e.g. twenty) sample tubes containing samples. The samples tubes may all have different geometries, caps and sample levels. FIG. 20B illustrates the light transmission measurements for each of the tubes illustrated in FIG. 20A. The identified cap region is illustrated with reference numeral 2000 in FIG. 20B.

2. Depth Measurement for Bottom Inlay

Bottom inlay may refer to the non-cylindrical section of a sample tube at the lower end. Precise measurement of the inlay depth may be important for correct calculation of the sample volume. On LLD measurement, the bottom inlay may be identified as the region linking the sample solution to the lower air layer. Due to strong light absorption in the sample solution and weak absorption in the air, the measurement value in the region of the bottom inlay, as shown in FIG. 20B, always starts at low (nearly the minimum of the entire measurement) and reaches high at the end (nearly the maximum of the measurement). While regions meeting this criterion is likely not unique on the entire measurement, the actual region representing the bottom inlay can be uniquely determined by confining the search in a narrow area which is below the detected sample top. The identified bottom inlays are illustrated with reference numeral 2002 in FIG. 20B.

3. Derivation of Tube Diameter

Upon determining the inlay type, the inner tube diameter may be determined next. For tubes having inlay of simple geometric shape, the inner tube diameter may be estimated directly from the longitudinal dimension of the inlay (i.e. the depth of the inlay). For example, for a hemispherical tube bottom, the transverse dimension (i.e. the inner tube diameter) is expected to be twice of the longitudinal dimension (i.e. the bottom height). For tubes having bottoms of complex geometry, the inner tube diameter may be determined using a lookup table storing the correspondence between the inlay type and the tube dimension.

4. Cap Classification

Figure 21A:
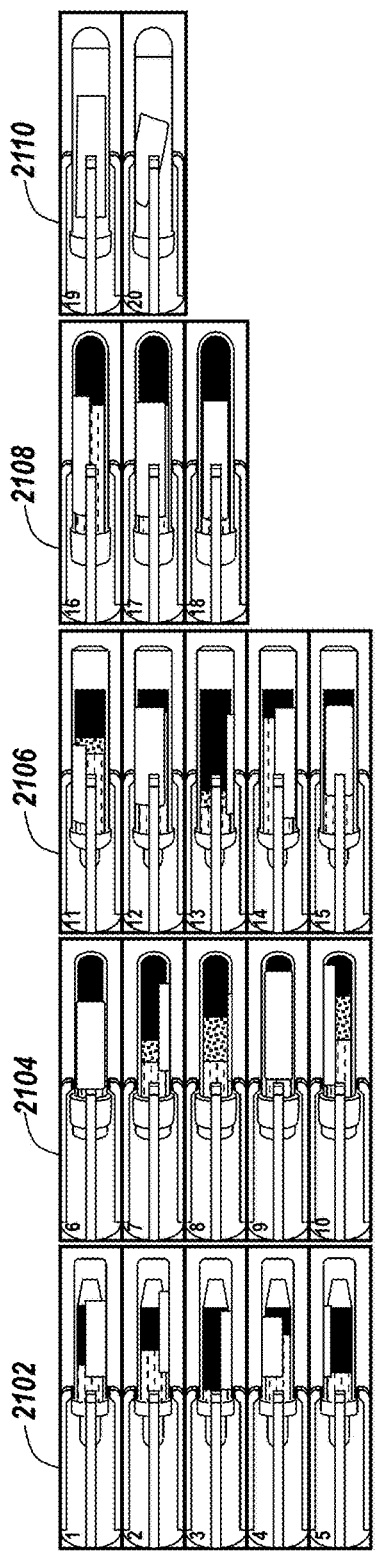
FIG. 21A illustrates various sample tubes grouped into different groups based on cap geometries, in one embodiment of the invention.
Figure 21B:
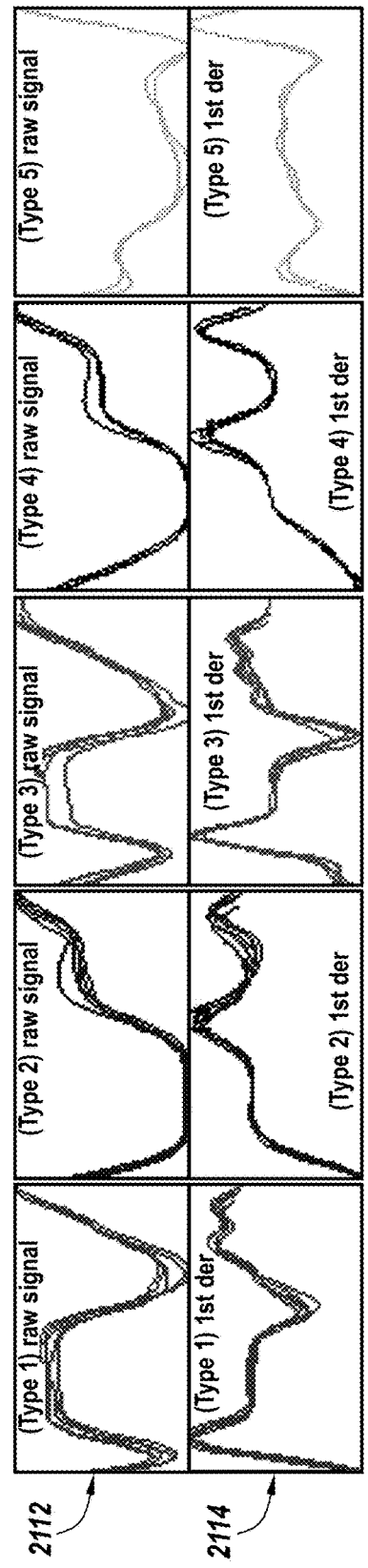
FIG. 21B illustrates raw LLD data and the $1^{st}$ derivative of the data associated with the cap geometries illustrated in FIG. 21A, in one embodiment of the invention.

Cap geometry is an important tube characteristic. FIG. 21A illustrates various sample tubes grouped into 5 different groups 2102, 2104, 2106, 2108 and 2110 based on cap geometries. Caps in each group have similar geometries (i.e. shapes). For each cap geometry, i.e. for each group 2102, 2104, 2106, 2108 and 2110, the corresponding LLD measurements present a specific and consistent pattern, as shown in FIG. 21B. The pattern is a result of the non-cylindrical shape of the cap, due to the variation of the absorption path length along the tube axis, and thus can be a signature of the cap geometry. This signature is represented by the raw LLD data illustrated in the first row of graphs 2112 and the $1^{st}$ derivative of the data illustrated in the second row of graphs 2114 as shown in FIG. 21B. By assessing the similarity of the signatures, the tubes can be sorted according to their cap shapes, e.g. type 1, type 2, type 3, type 4 and type 5. A quantitative measurement of the similarity of two signals u and v is the normalized inner product of the signals, calculated as:

$$\frac{\overline{u} \cdot \overline{v}}{|\overline{u}||\overline{v}|}$$

Each signal may be represented by a vector in a high-dimensional space. That is, an array of transmission values, corresponding to defined vertical positions, may be created for each tube. For example, if 2 mm steps values are assigned to the tubes, the longer tubes would have more values, thus leading to a higher vector dimension. The signal values determine the vector position and the signal length determines the dimensions of the vector space. Since the cap height varies from one cap type to another, the compared signals may not be at equal length. In such case, the relatively short signal should be padded with zero values at the lower end of the signal to be aligned with the longer one for vector operation purposes. With such matching operation, information of the cap height can be preserved in the measurement of signal similarity.

Figure 22A:
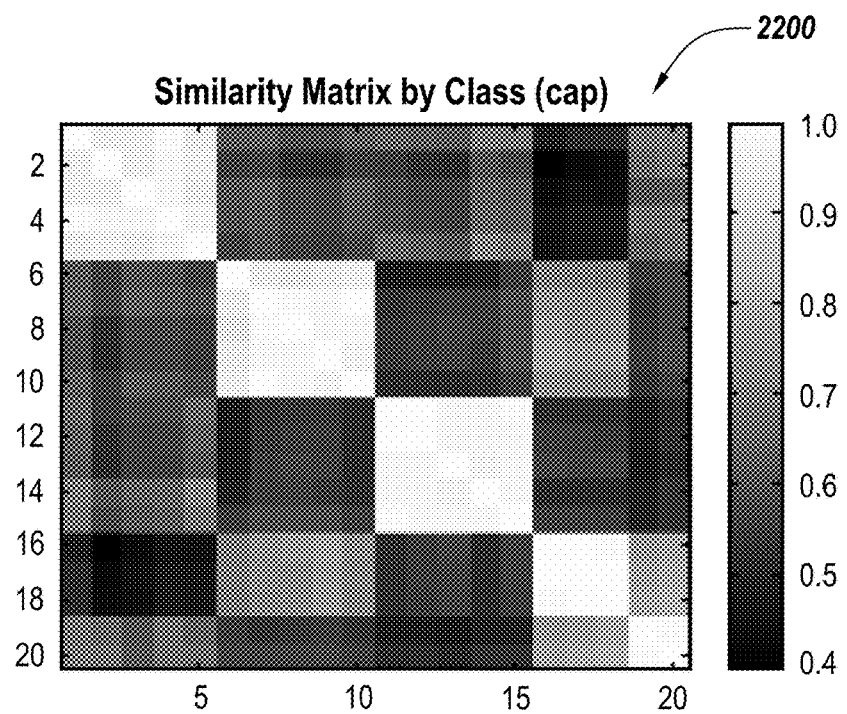
FIG. 22A illustrates a gray map depicting similarity scores computed for the cap geometries illustrated in FIG. 21A, in one embodiment of the invention.
Figure 22B:
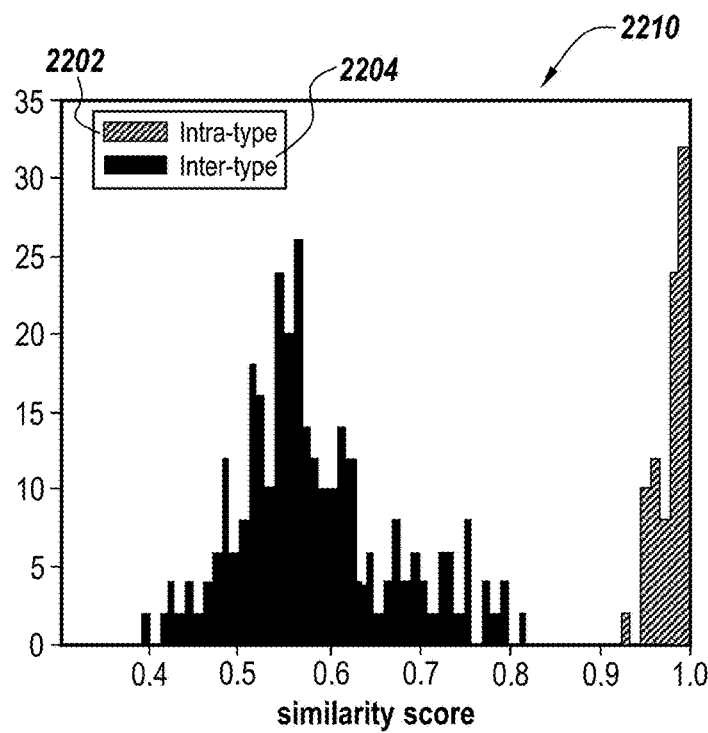
FIG. 22B illustrates distribution of the similarity scores computed for the cap geometries illustrated in FIG. 21A, in one embodiment of the invention.

Besides signal similarity, the similarity of the signal changes may also be evaluated. The weighted sum of these two similarity quantities can then be used as a metric for evaluating the probability of the compared caps being the same type: the higher the weighted sum the more likely the caps are the same type. The similarity scores are computed for the caps illustrated in FIG. 21A and shown in a gray map 2200 illustrated in FIG. 22A. The coordinate axes of the map 2200 represent tube indices (e.g. an index for each one of the 20 tubes illustrated in FIG. 21A). As it can be seen from the map 2200, the inter-type scores are at relatively higher values (e.g. white areas in the diagonal) than the intra-type scores. Similarly, the intra-type score of similarity is higher than the inter-type scores. FIG. 22B illustrates the distribution of the similarity score 2210. As shown in FIG. 22B, the two types of scores (i.e. the inter-type scores 2204 and the intra-type scores 2202) are well separated. FIG. 22B manifests that the similarities score is a good numerical metric for differentiating the different cap geometries.

The cap classification discussed above in connection with FIGS. 21A-22B may be used to generate a database that contains the signature template of each cap type that may be used on the instrument. The database may be updated when a new cap type becomes available. When a sample tube is being analyzed on the instrument, its cap signature may be compared with all the cap signature templates in the database. The sample tube may be assigned a cap type whose signature has the highest similarity to the cap signature of the sample tube.

5. Classification of Bottom Inlay

Figure 23A:
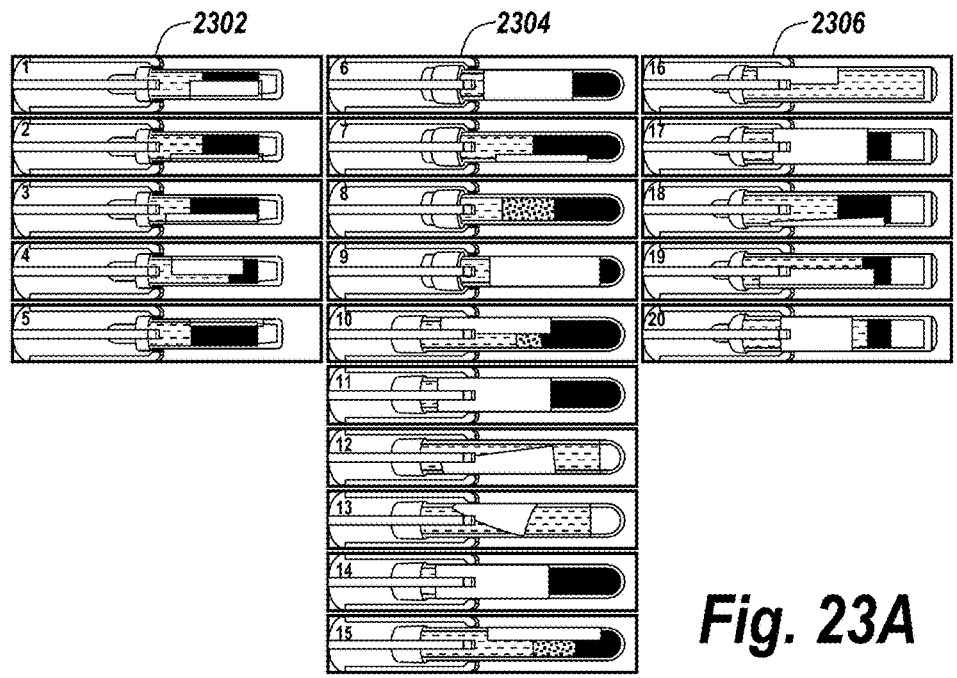
FIG. 23A illustrates various sample tubes grouped into different groups based on inlay geometries, in one embodiment of the invention.
Figure 23B:
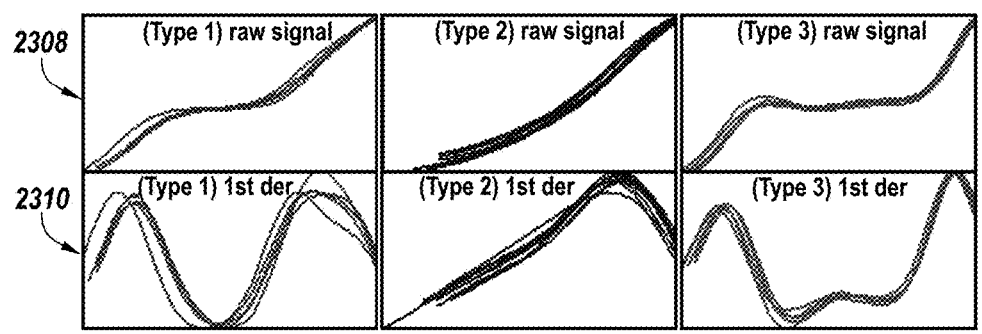
FIG. 23B illustrates raw LLD data and the $1^{st}$ derivative of the data associated with the inlay geometries illustrated in FIG. 23A, in one embodiment of the invention.

Similar to the tube cap, measurement of the bottom inlays present patterns that change with inlay shapes. The bottom inlays may be sorted using the same or similar method used for classifying caps. The method may be modified when the normalized inner product is computed. With the bottom inlay classification, the signal segments should be aligned to their right and zero-padded on the left, since the lower edge of the tube bottom may be determined more accurately and reliably. For demonstration purposes, the same set of sample tubes shown in FIG. 21A is re-sorted according to inlay geometry in FIG. 23A. As illustrated in FIG. 23A, the tubes may be grouped into three groups 2302, 2304, 2306 corresponding to three different types of bottom inlay. Each of the bottom inlay types may have a unique signature in raw data illustrated in the first row of graphs 2308 and 1st derivative signals illustrated in the second row of graphs 2310, as shown in FIG. 23B.

Figure 24A:
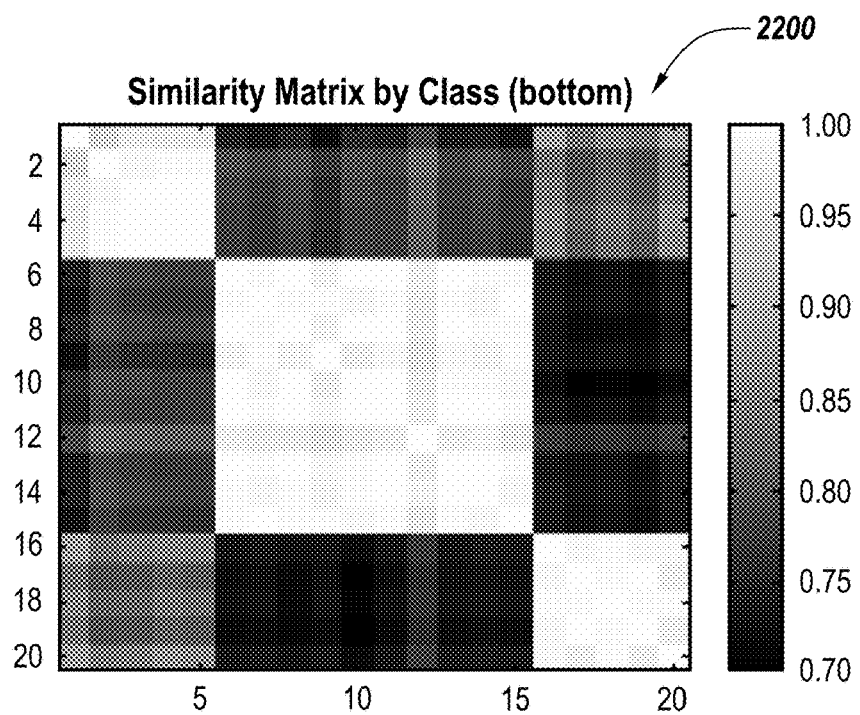
FIG. 24A illustrates a gray map depicting similarity scores computed for the inlay geometries illustrated in FIG. 23A, in one embodiment of the invention.
Figure 24B:
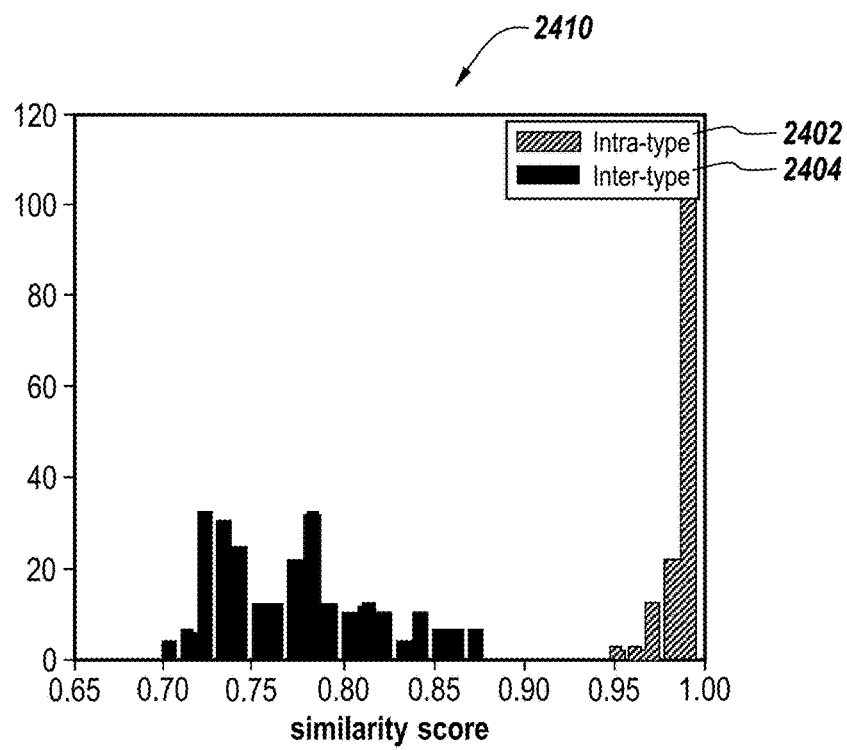
FIG. 24B illustrates distribution of the similarity scores computed for the inlay geometries illustrated in FIG. 23A, in one embodiment of the invention.

Besides signal similarity, the similarity of the signal changes may also be evaluated. The weighted sum of these two similarity quantities can then be used as a metric for evaluating the probability of the compared bottom inlays being the same type: the higher the weighted sum the more likely the bottom inlays are the same type. The similarity scores are computed for bottom inlays in the set of sample tubes (e.g. twenty sample tubes illustrated in FIG. 23A) and shown in a gray map 2400 illustrated in FIG. 24A. The coordinate axes of the map 2400 represent tube indices (e.g. an index for each one of the 20 tubes illustrated in FIG. 21A). As it can be seen from the map 2400, the inter-type scores are at relatively higher values (e.g. white areas in the diagonal) than the intra-type scores. FIG. 24B illustrates the distribution of the similarity score 2410. As shown in FIG. 24B, the two types of scores (i.e. the inter-type scores 2404 and the intra-type scores 2402) are well separated. FIG. 24B manifests that similarities score is a good numerical metric to differentiate different bottom inlays.

Similar to the case of cap classification, a database containing the signature template of each bottom type may be generated. The database may be updated when a new bottom type becomes available. When a sample tube is being analyzed on the instrument, its bottom signature may be compared with all the bottom signature templates in the database. The sample tube may be assigned a bottom type whose signature has the highest similarity to the bottom type signature of the sample tube.

The various participants and elements described herein with reference to the figures may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Figure 25:
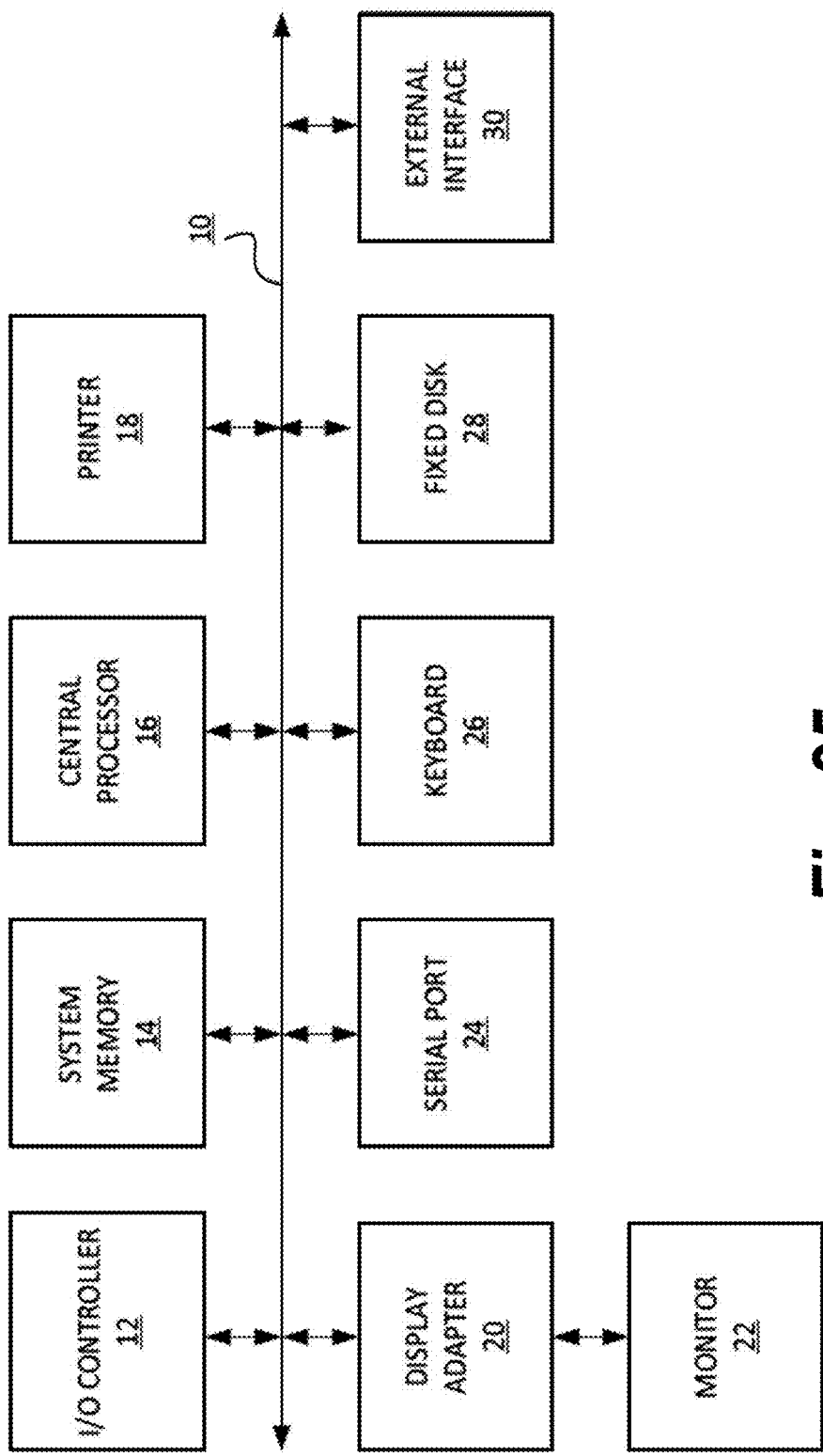
FIG. 25 illustrates a block diagram of an exemplary computer apparatus.

Examples of such subsystems or components are shown in FIG. 25. The subsystems shown in FIG. 25 are interconnected via a system bus 10. Additional subsystems such as a printer 18, keyboard 26, fixed disk 28 (or other memory comprising computer readable media), monitor 22, which is coupled to display adapter 20, and others are shown. Peripherals and input/output (I/O) devices, which couple to I/O controller 12 (which can be a processor or other suitable controller), can be connected to the computer system by any number of means known in the art, such as serial port 24. For example, serial port 24 or external interface 30 can be used to connect the computer apparatus to a wide area network such as the Internet, a mouse input device, or a scanner. The interconnection via system bus allows the central processor 16 to communicate with each subsystem and to control the execution of instructions from system memory 14 or the fixed disk 28, as well as the exchange of information between subsystems. The system memory 14 and/or the fixed disk 28 may embody a computer readable medium.

Embodiments of the technology are not limited to the above-described embodiments. Specific details regarding some of the above-described aspects are provided above. The specific details of the specific aspects may be combined in any suitable manner without departing from the spirit and scope of embodiments of the technology. For example, back end processing, data analysis, data collection, and other processes may all be combined in some embodiments of the technology. However, other embodiments of the technology may be directed to specific embodiments relating to each individual aspect, or specific combinations of these individual aspects.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method comprising:
  receiving, by a processor, container identification data from a container inspection unit that analyzes a container containing a liquid;
  determining, by a liquid level detection unit, liquid level detection raw data including a height of a liquid content layer within the container by rotating the container about a z-axis of the container as the container is held by a robotic arm, and obtaining multiple angular readings of the liquid around the container;
  receiving, by the processor, the liquid level detection raw data from the liquid level detection unit that analyzes the container containing the liquid;
  determining a liquid level detection result for the liquid in the container, based at least on the container identification data and the liquid level detection raw data;

receiving, by the processor, additional data from the container inspection unit;

cross-checking, by the processor, the liquid level detection result with the additional data received from the container inspection unit; and determining if the liquid level detection result is erroneous as a result of the cross-checking.

2. The method of claim 1 further comprising:

generating, by the processor, a combined result of the container inspection unit and the liquid level detection unit after cross-checking the liquid level detection result.

3. The method of claim 2 wherein the combined result includes volume information, content confirmation, liquid layers, a gel position, a spun state, a serum/cruor ratio and error states.

4. The method of claim 1 wherein the container is a tube comprising a cap, and the container inspection unit is a tube inspection unit.

5. The method of claim 1 wherein the liquid level detection unit executes one or more of a serum/urine detection algorithm, a gel detection algorithm, a cruor detection algorithm and a whole blood detection algorithm.

6. The method claim 1 wherein the liquid level detection unit comprises a device that measures the height of the liquid content layer in the container by transmitting radiation through the container.

7. The method of claim 1 wherein the container inspection unit comprises a camera.

8. The method of claim 1 the liquid level detection result includes a liquid level and a sample volume.

9. The method of claim 1 wherein the container identification data comprises one or more of an inner diameter, an outer diameter, a height, a height without cap, a color pattern side, a color pattern top, a top rubber (inner) diameter, a decapping profile, a liquid level height offset, a "calculate no volume" flag, a cap material type, a "tube has thread" flag, a "cap pierce through" flag, a "contains gel" flag, a bottom shape, an expected gel height, a sample type, a false bottom (inlay), a conicity/tapering flag, a translucent flag, or a draw volume of the container.

10. The method of claim 1, wherein the liquid contains serum and gel, and wherein an interface between the serum and the gel is at an angle relative to a vertical axis of the container.

11. The method of claim 1, wherein the multiple angular readings of the liquid around the container are obtained using multiple pairs of light sources and light detectors.

12. The method of claim 1 wherein the robotic arm has at least three prongs which grip the container.

13. The method of claim 1 wherein the container is vertical as it is rotated.

14. The method of claim 1 wherein the multiple angular readings is ten angular readings.

15. A computer comprising:

a processor; and a computer readable medium coupled to the processor, the computer readable medium comprising code, executable by the processor, to implement a method comprising:

receiving container identification data from a container inspection unit that analyzes a container containing a liquid;

determining, by a liquid level detection unit, liquid level detection raw data including a height of a liquid content layer within the container by rotating the container about a z-axis of the container as the container is held by a robotic arm, and obtaining multiple angular readings of the liquid around the container;

receiving the liquid level detection raw data from the liquid level detection unit that analyzes the container containing the liquid;

determining a liquid level detection result for the liquid in the container, based at least on the container identification data and the liquid level detection raw data;

receiving, by the processor, additional data from the container inspection unit;

cross-checking, by the processor, the liquid level detection result with the additional data received from the container inspection unit; and determining if the liquid level detection result is erroneous as a result of the cross-checking.

16. The computer of claim 15 wherein the method further comprises:

generating a combined result of the container inspection unit and the liquid level detection unit after cross-checking the liquid level detection result.

17. The computer of claim 15 wherein the liquid level detection unit executes one or more of a serum/urine detection algorithm, a gel detection algorithm, a cruor detection algorithm and a whole blood detection algorithm.

18. A system comprising:

the computer of claim 15;

the container inspection unit coupled to the computer; and the liquid level detection unit coupled to the computer.

19. The system of claim 18 wherein the method further comprises generating a combined result of the container inspection unit and the liquid level detection unit after cross-checking the liquid level detection result.

20. The system of claim 19 wherein the method further comprises:

distributing the combined result to one or more additional units coupled to the computer.

21. The system of claim 20 wherein the additional units include a centrifuge unit, a decapper unit, a recapper unit, an aliquotter unit, an analyzer unit and an output unit.

22. The system of claim 19 wherein the combined result includes a volume, content confirmation, layers of the liquid, a gel position, a spun state, a serum/cruor ratio, a container identifier, a cap identifier, a cap color identifier and error states.

* * * * *